United States Patent
Jin

(10) Patent No.: US 10,646,409 B2
(45) Date of Patent: May 12, 2020

(54) COMPOSITIONS AND METHOD FOR VISCOSITY-INCREASABLE DENTAL COMPOSITES

(71) Applicant: DENTSPLY SIRONA Inc., York, PA (US)

(72) Inventor: Xiaoming Jin, Middletown, DE (US)

(73) Assignee: DENTSPLY SIRONA INC., York, PA (US)

( * ) Notice: Subject to any disclaimer, the term of this patent is extended or adjusted under 35 U.S.C. 154(b) by 140 days.

(21) Appl. No.: 15/904,919

(22) Filed: Feb. 26, 2018

(65) Prior Publication Data

US 2018/0250201 A1    Sep. 6, 2018

Related U.S. Application Data

(60) Provisional application No. 62/466,431, filed on Mar. 3, 2017.

(51) Int. Cl.
| | |
|---|---|
| *A61K 6/083* | (2006.01) |
| *A61K 6/887* | (2020.01) |
| *A61K 6/17* | (2020.01) |
| *A61K 6/61* | (2020.01) |
| *A61K 6/62* | (2020.01) |
| *A61K 6/77* | (2020.01) |
| *A61K 6/838* | (2020.01) |
| *A61K 6/871* | (2020.01) |
| *A61K 6/891* | (2020.01) |

(52) U.S. Cl.
CPC ............... *A61K 6/887* (2020.01); *A61K 6/17* (2020.01); *A61K 6/61* (2020.01); *A61K 6/62* (2020.01); *A61K 6/77* (2020.01); *A61K 6/838* (2020.01); *A61K 6/871* (2020.01); *A61K 6/891* (2020.01)

(58) Field of Classification Search
CPC ....................................................... A61K 6/083
See application file for complete search history.

(56) References Cited

U.S. PATENT DOCUMENTS

| | | | | |
|---|---|---|---|---|
| 5,100,929 A | * | 3/1992 | Jochum | A61K 6/0017 522/180 |
| 6,652,281 B1 | * | 11/2003 | Eckhardt | A61K 6/083 433/217.1 |
| 2017/0022414 A1 | * | 1/2017 | Boogaerts | C08K 5/0008 |

FOREIGN PATENT DOCUMENTS

DE    3837569 A1 *  5/1990  ........... A61K 6/0017

* cited by examiner

*Primary Examiner* — Michael F Pepitone
(74) *Attorney, Agent, or Firm* — Dentsply Sirona Inc

(57) ABSTRACT

Described is a stable, two-component low viscosity composite that is capable to achieve excellent adaptation to walls/substrates due to its intrinsic flow ability and is also capable of rapid viscosity increasing and being manipulated prior to cure by light upon mixing of such a two-paste composite due to one distinguished reaction promoting partial network formation thus to allow a practitioner further manipulate a firm composite. Upon a completed manipulation by the practitioner, such a mixed material should be readily cured into final solid form by using conventional curing light.

12 Claims, 17 Drawing Sheets

Initiation

Propagation (polar solvent)

Propagation (non-polar solvent)

Top row: as-delivered or as-mixed
Middle row: during first 30 seconds upon initial delivery
Bottom row: at the 5th minute post initial delivery Series 1: Initial Complex Viscosity
Series 2: Complex Viscosity @ 10min
Series 3: Initial Storage Modulus
Series 4: Storage Modulus @ 10min

COMPOSITIONS AND METHOD FOR VISCOSITY-INCREASABLE DENTAL COMPOSITES

TECHNICAL FIELD

Disclosed herein is a two-component flowable composite that is intrinsically capable of adapting to tooth substrates. In addition, by incorporating a "Chemical Thickener" in two-component flowable compositions, of which would allow two orthogonal chemistries, nucleophile-initiated thiol/ene Michael addition and light-initiated radical polymerization to proceed sequentially. Thus it could to offer the advantage of further manipulation on such thickening paste with adequate working time prior to final curing by light.

BACKGROUND

SureFil SDRflow® set up as a standard for bulk-fill flowable as easy to use and excellent adaption due to its lower viscosity, lower curing stress and high depth of cure. However, it seems highly desirable if it can be further manipulated by the clinicians although the low viscosity make possible to achieve the best adaption, which is critical to minimize the failure of the bulk restoration. Therefore, in order to improve the SureFil SDRflow® while carry its signature feature of self-leveling, a possible phase change from lower viscosity to higher viscosity become a new twist. It is expected that this would be able to effectively balance between adaptation and manipulation.

A flowable composite should be able to undergo a rheological phase change from low viscosity to a firm paste upon a paste/paste mixing. Several approaches were proposed based on either chemistry and/or technology. If a chemistry could allow a selective cure for part of formulated material to building up its texture (viscosity) in given time, it should be possible to develop such a viscosity-increasable flowable that should delivery some feature we would like. For instance, a chemical approach can be based on a sequential curing mechanism, from which distinguished chain growth and network-formation are involved in. Consequently the initial paste offer lower viscosity for achieving good adaptation and then first curing mechanist is triggered for viscosity building-up but would not cause unnecessary cross-linking. Finally cross-linking is kicked in by light irradiation for strengthening the performance.

ABBREVIATION KEY

Figure 1:
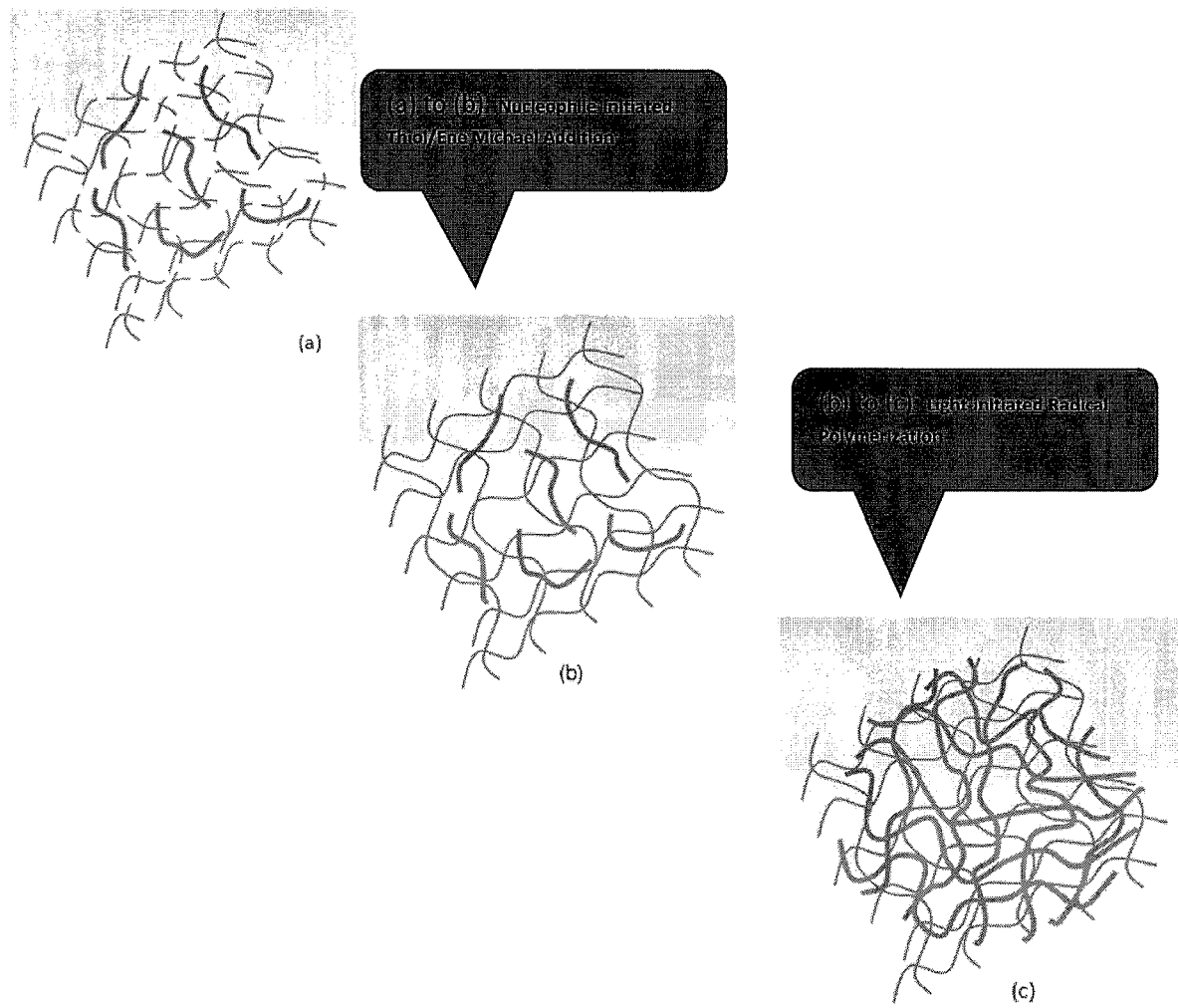
FIG. 1 is a schematic of an in situ interpenetrating polymer network process with orthogonal chemistries.

TEGDMA: tri(ethylene glycol) dimethacrylate
EDAB: ethyl 4-(dimethylamino) benzoate
PETMP: Pentaerythritol Tetra(3-mercaptopropionate)
ETTMP: Ethoxilated-Trimethylolpropan Tri(3-Mercaptopropionate)
EBPADMA: ethoxylated bisphenol-A dimethacrylate
TCDCDA: Tricyclo[$5.2.1.0^{2,6}$]decanedimethanol diacrylate
CQ: camphorquinone
LTPO: 2,4,6-trimethylbenzoyl-diphenyl-phosphine oxide
BHT: Butylated hydroxytoluene
BAFG: barium-alumino fluoroborosilicate glass
DBU: 1,8-Diazabicyclo[5.4.0]undec-7-ene
DBN: 1,5-Diazabicyclo[4.3.0]non-5-ene
TEA: triethylamine
PYG: Pyrogallol
TPP: Triphenyl phosphite
DABCO: 1,4-diazabicyclo[2,2,2]-octane
Test Methods:
NMR Analysis: Nuclear magnetic resonance (NMR) spectra were recorded on a Varian 300 MHz spectrometer.

Samples were prepared in CDCl₃ at ca. 15% v/v. Chemical shifts are reported in parts per million (ppm) relative to TMS.

FTIR Analysis: Fourier transform infrared spectra (FTIR/ATR) were recorded on a Thermo Electron Nicolet 6700 Spectrometer.

Photo DSC: Differential Scanning calorimeter (Q2000, TA Instrument) with photocalorimetry accessory (PCA), from which UV/Visible light (250-650 nm) from a 200 W high pressure mercury source is transmitted to the sample chamber via an extended range, dual-quartz light guide with neutral density or band pass filters, was used to evaluate the photolysis and photopolymerization for the neat resin and/or any formulated resin system. Under both air and nitrogen, the test was performed. The light outputs and light spectrum can be tuned by using build-in filter, or additional UV filter or intensity-reducing filter.

Flexural strength and modulus are tested according to ISO 4049, 2×2×25 mm specimens were cured by three overlapped spot curing with Spectrum 800 with 13 mm light guide at 800 mw/cm², 20" for each spot on one side only. The cured specimens (6-10) were placed in DI water and stored at 37° C. for 24 hrs, then were sanded prior to the test at room temperature.

Compressive strength and modulus are tested according to ISO 9917, which is actually for water-based cements since ISO 4049 does not specify for compressive strength. ϕ4×6 mm glass slave as mold for specimen preparation (6). It was cured by Spectrum 800 at 800 mw/cm² from both top and bottom, at 20" each. The cured specimens (6-10) were placed in DI water and stored at 37° C. for 24 hrs, and then were sanded prior to the test at room temperature.

Shrinkage Stress was measured by using NIST/ADA's tensometer. Specimen with 2.25 mm in thickness (c-factor as 1.33) is cured for 60 seconds by DENTSPLY/Caulk's QHL light at 550 mw/cm2. The total stress at the $60^{th}$ minute is taken to rank different materials.

Rheology property was measured by using TA's DHR Rheometer. ϕ40 mm 2° geometry is used for resin viscosity measurement and ϕ20 mm flat geometry was used for composite's evaluation. Oscillation test is set up at 175 Ps shear stress, 1 Hz shear frequency at 35° C.

Ross planetary mixer (120 F/20 in psi), SpeedMix (RT) and Resodyn (RT/20 In psi) are used in prepared filler blend and resin mixture and the flowable composite pastes.

digi syringe system with auto mixing tip was used to pack the individual base paste and catalyst paste, respectively.

DETAILED DESCRIPTION

There are different approaches based on either chemistry and/or technology in creating a viscosity-increasable flowable composite. If chemistry could allow a selective reaction for part of a formulated material to building up its texture (viscosity) in given time, it should be possible to develop such a viscosity-increasable flowable that should delivery some desirable features. For instance, a chemical approach can be based on a sequential curing mechanism, from which distinguished chain growth and network-formation are involved in. Consequently the initial paste offers lower viscosity for achieving good adaptation and then a first curing mechanism is triggered for viscosity building-up but would not cause unnecessary cross-linking. Finally cross-linking is initiated by light irradiation for strengthening the performance.

One example of conventional approach was based on a polyacid/polybase for such viscosity-increasing process, which was indeed able to promote viscosity increasing via non-radical reaction. It was found that the pair of acid/base in structure and composition would impact significantly on the viscosity profile and mechanical property. 10-MDP and Penta appear more effective to react with polyimidazole. Polyacrylic acid showed limited reactivity towards polyimidazole in absence of water. In addition, as expected, a significant increase in water absorption in all cured composites were found, which led to decrease in mechanical strength in wet specimen.

The potential benefits, however, are the improved moisture tolerant as such increased hydrophilicity. In addition, there was also challenge to achieve really good initial adaptation of the resulting as-mixed composite as required from the low viscosity and rapid viscosity increase to allow some kind manipulation plus offer adequate mechanical properties. It should be possible to achieve a balance between viscosity change and paste manipulation but it is also realized that it is remain very challenge for achieving superior mechanical strength as universal composite due to its intrinsic low filler loading without a significant change in filler. In order to achieve a rapid viscosity building-up, new polybase or polyacid resins or reactive filler might be necessary.

Figure 2:
FIG. 2 demonstrates a mechanism for the base-catalyzed thiol-Michael addition reaction.
Figure 2:
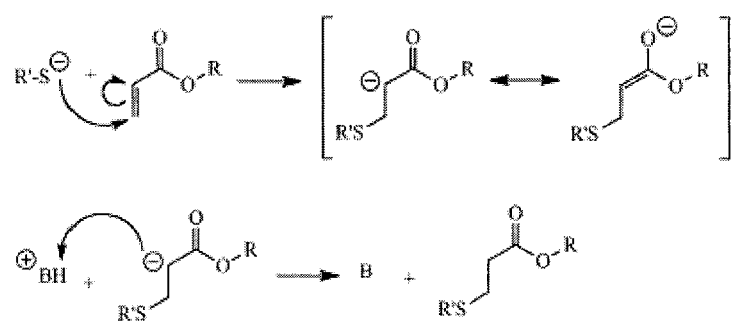
Figure 2:
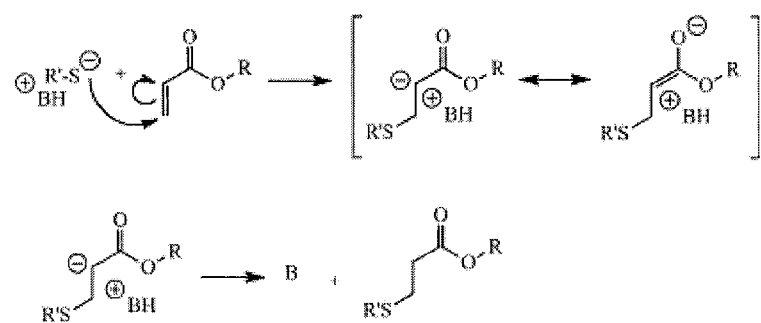

Another possible approach to realizing a dual-cure, viscosity-increasing process as described in the present disclosure would be a thiol/ene-based cure for initial chain extension for viscosity building-up while the paste remain as workable/manipulatable, then light irradiation to lead a fully cured material. It was expected that such two distinct chemistries would afford two-stage curing process so as to balance the adequate initial adaptation and subsequent manipulation from a single material. In addition, it was also expected that his approach would address the issues that were noticed in the conventional polyacid/polybase process, such as the increasing water absorption for inferior mechanical properties, relatively slow reaction and an initial higher viscosity. Chris Bowman's team at University of Colorado reported two-stage reactive polymer network forming systems, in which a base-catalyzed thiol-ene addition was set up for initial curing process and photo-initiated light curing to finalize the entire networking process, as shown in FIG. 2. Such chemistry might work for our intended viscosity-increasing flowable composition. However, the thiol-ene reaction is too slow to generate significant viscosity building up. Though a highly reactive super base (1, 8-diazabicyclo[5,4,0]undec-7-ene, DBU) could be used to accelerated the thiol/ene reaction, it was discovered it would also even trigger the methacrylate/thiol reaction for most methacrylate pair we tested, especially for those urethane-based methacrylate resins.

From our comprehensive investigation on such thiol/ene systems, it was further discovered a remarkably stable pair that is composed of dimethacrylate and polythiol, more specifically EBPADMA and PETMP, which would allow to formulate a stable base paste. Furthermore, a viscosity-increasing flowable should be readily resulted from a catalyst paste that is composed of methacrylate resin polyacrylate resins, photoinitiators for the $2^{nd}$ step curing; and the catalysts of thiol/ene addition, DBU and a base paste that is composed of polythiol and methacrylate matrix.

Figure 3:
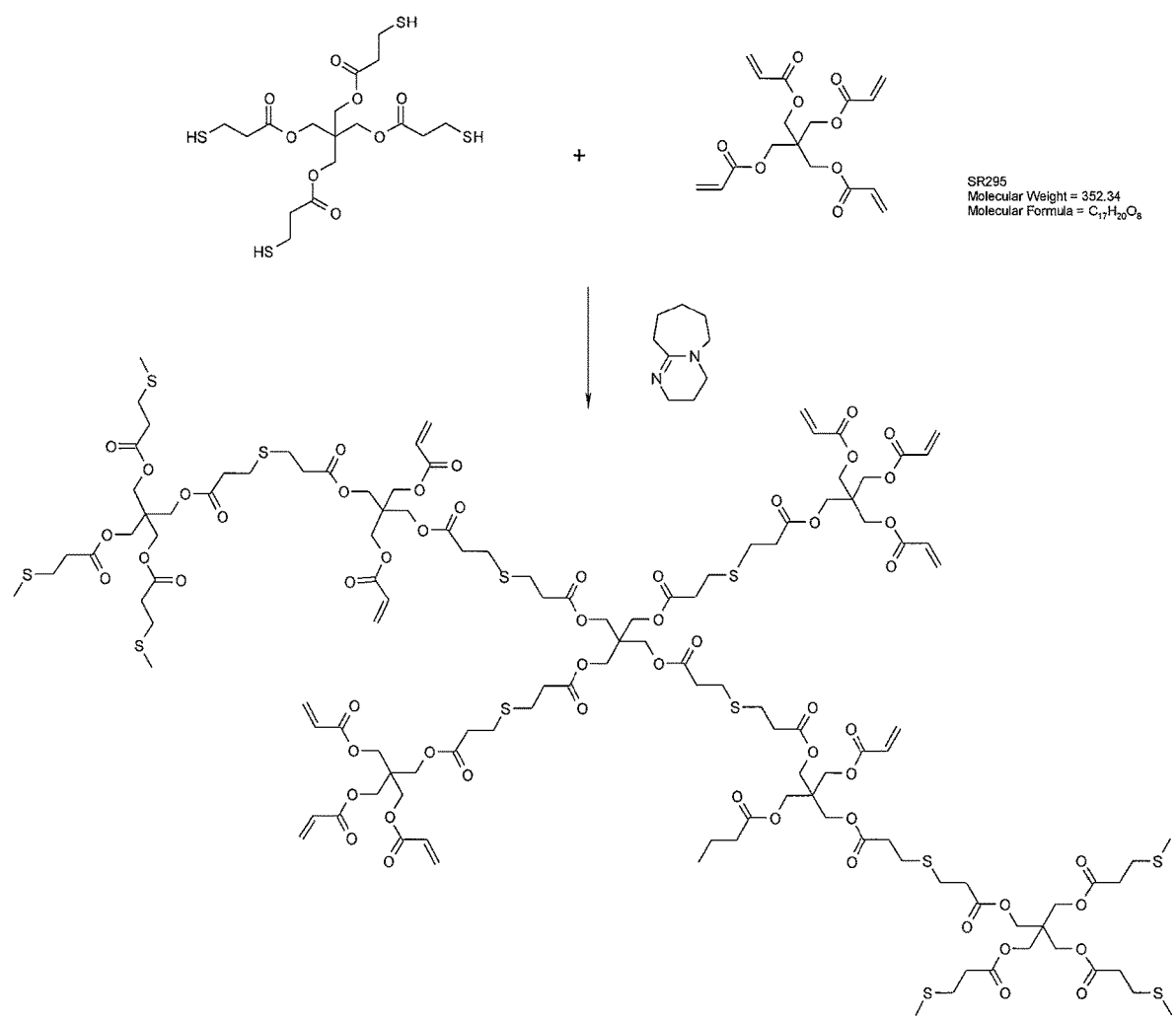
FIG. 3 demonstrates a thiol/ene reaction to network formation based on PETMP and TCDCDA in the presence of DBU.
Figure 4:
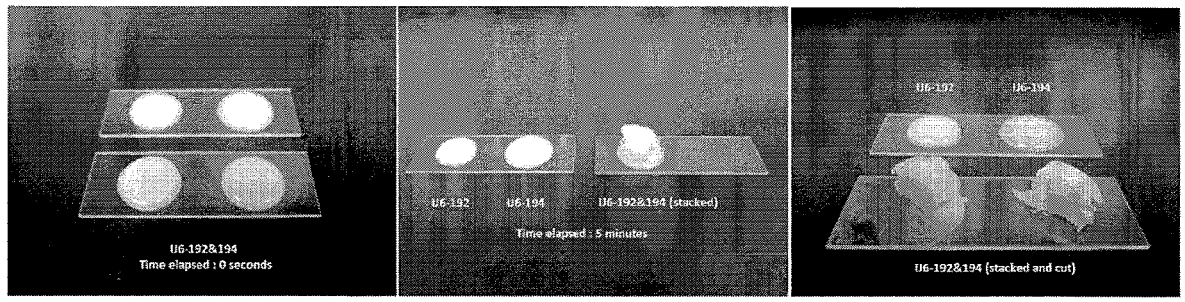
FIG. 4 is a visual illustration of the viscosity increasing composite as dual-cure with unlimited working time demonstrating that the viscosity increased as quickly as five minutes.
Figure 5:
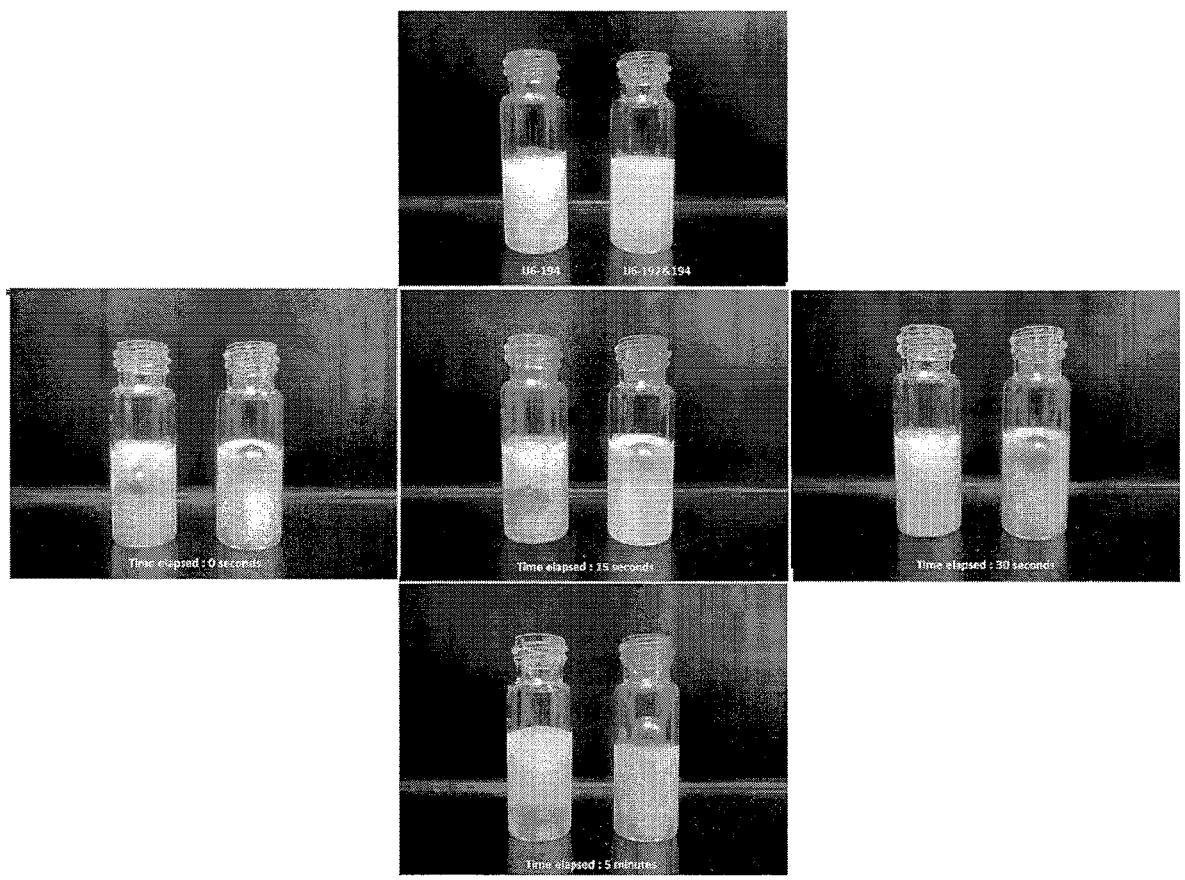
FIG. 5 shows paste status as different times for an individual paste and a paste/paste mix according to the present disclosure with a metal bearing therein to show the increase in viscosity. The individual paste is on the left of each picture, while the paste/paste mix is shown on the right. As seen from these pictures, the paste/paste mix increases in viscosity at a much faster rate an individual paste alone.
Figure 6:
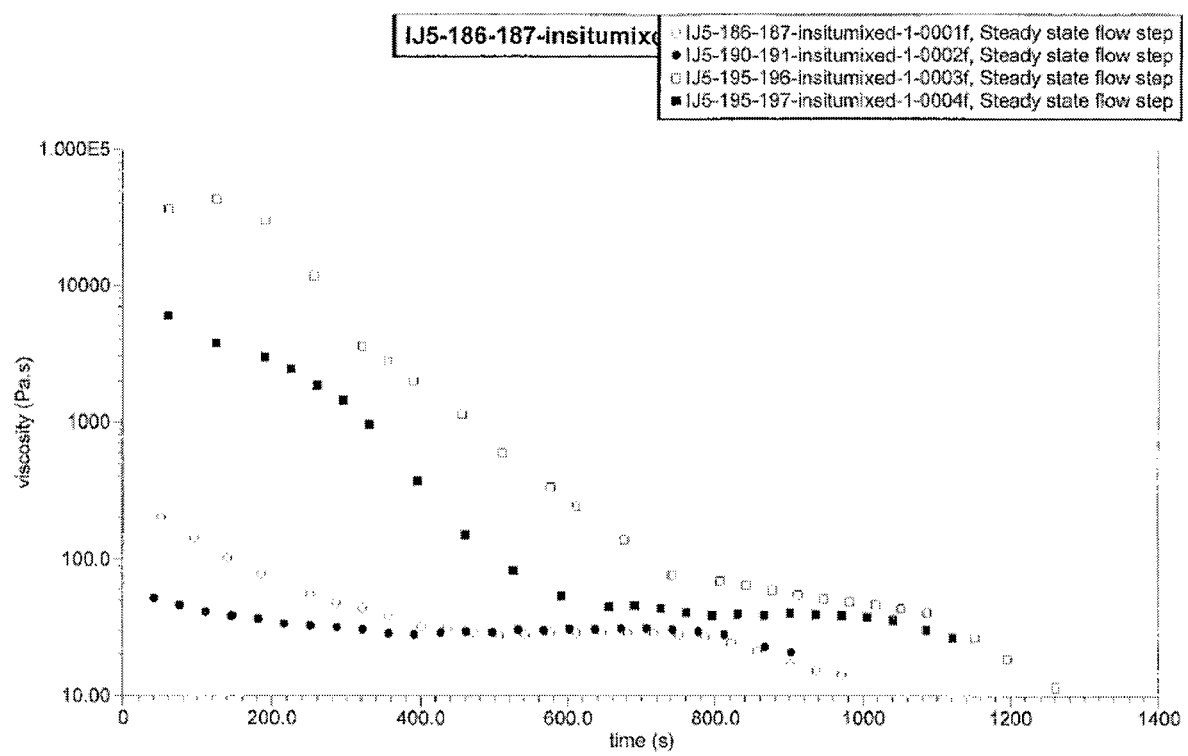
FIG. 6 demonstrates the effect of reactive acrylate resins on the initial viscosity of mixed composites.
Figure 7:
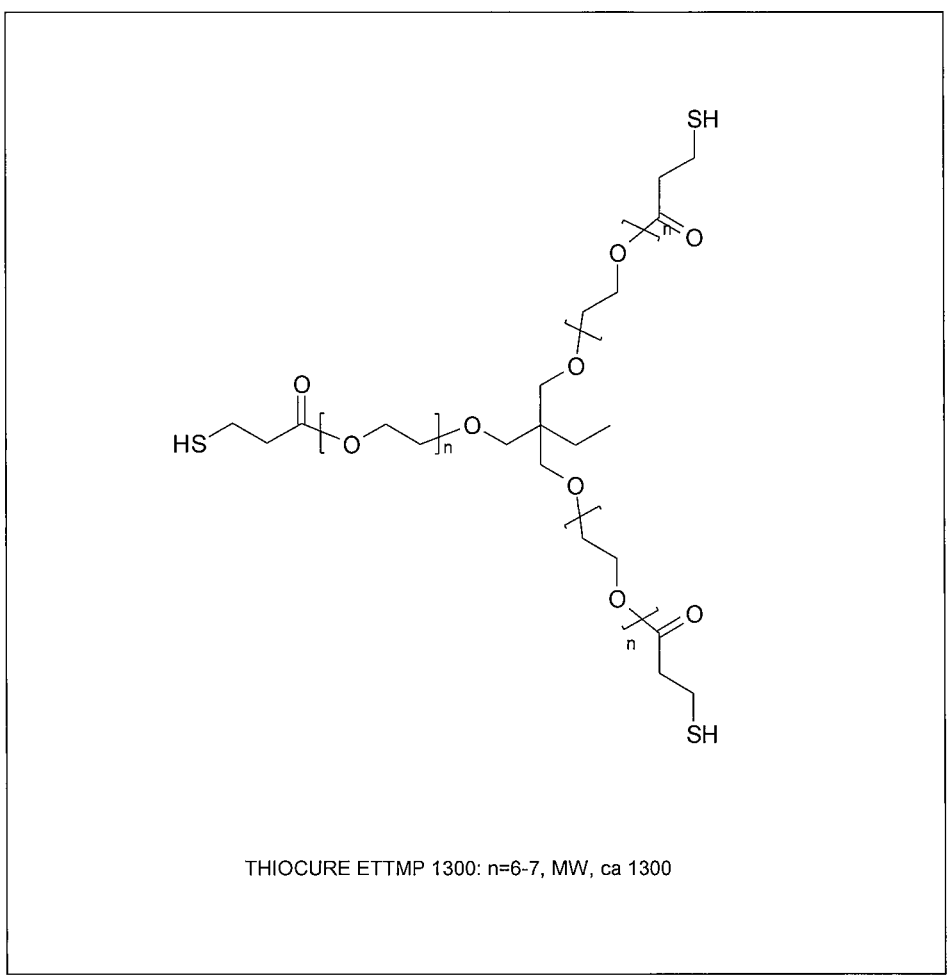
FIG. 7 is a schematic of a molecular structure of Ethoxylated-Trimethylolpropane Tri(3-Mercaptopropionate).
Figure 8:
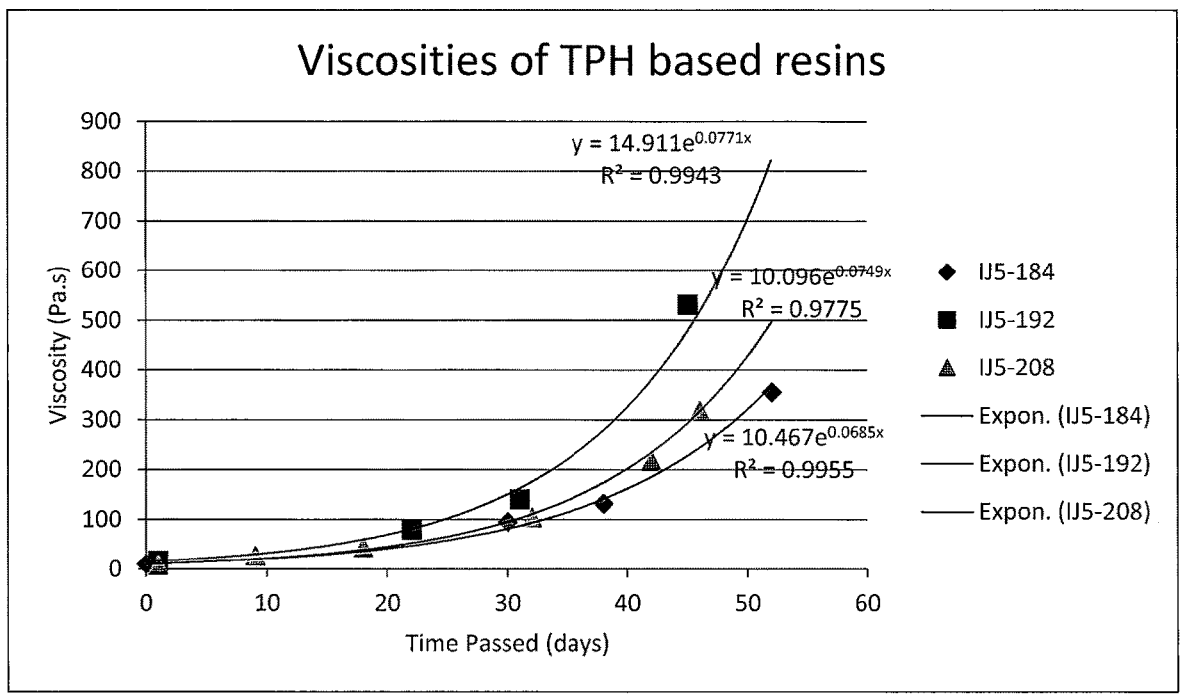
FIG. 8 shows the aging effect on viscosity of a conventional TPH® resin system.

As an example, it was illustrated in FIG. 3, a tetrathiol (PETMP) could be used as polythiol and a diacrylate (TCD-CDA) or a tetra-acrylate (SR295) was used as polyacrylate, and various bases could be used as catalyst, including triethyl amine (TEA), 1,8-diazabicyclo[5,4,0] undec-7-ene (DBU), and 1,4-diazabicyclo[2,2,2]-octane (DABCO).

As shown in Table 1 when the resin compositions of polythiol resin (PETMP) and polyacrylate resin (TCDCDA or SR295) varied, the speed of viscosity increasing upon mixing the resin blend of PETMP in TPH resin and TCD-CDA or SR295 in TPH Resin would change dramatically depending upon the the nature of the base catalyst (DBU, TEA and DABCO). Thus it did indicate that thiol-ene chemistry appears to proceed well and feasible to trigger the stage one network forming process for a viscosity-increasing composite without involving any radical polymerization. It was further found that only 0.3-0.4% of DBU is necessary to have a reasonable networking process for PETMP/TCD-CDA system, from which DBU was discovered as the most effective catalyst for such thiol/ene reaction.

TABLE 1

Compositions Effect on Speed of Gelation of Various Thiol-ene Resin Systems

| Sample ID | Polythiols mol PETMP | Polyacrylate mol TCDCDA | SR295 | Base Catalyst wt. % DBU | TEA | DABCO | Gelation Time |
|---|---|---|---|---|---|---|---|
| XJ9-176-1 | 0.01 | 0.02 | 0 | 0.8 | 0 | 0 | Instantly solidified |
| XJ9-176-2 | 0.01 | 0.02 | 0 | 0 | 0.8 | 0 | 3 hours |
| IJ5-170 | 0.01 | 0.02 | | 0.1 | 0.2 | | 4.5 hrs |
| IJ5-171 | 0.01 | 0.02 | | 0.2 | | | slower |
| IJ5-172 | 0.01 | 0.02 | | 0.2 | 0.4 | | 1 hr |
| IJ5-173 | 0.01 | 0.03 | | 0.3 | | | little faster |
| IJ5-174 | 0.01 | 0.04 | | 0.2 | 0.4 | | 4.5 hrs |
| IJ5-175 | 0.01 | 0.04 | | 0.4 | | | Instantly gelation |
| IJ5-176 | 0.01 | 0.02 | | 0.2 | 0.2 | | 3.5 hrs |
| IJ5-177 | 0.01 | | 0.02 | 0.2 | | | 3-18 hrs |
| IJ5-178 | 0.01 | 0.03 | | 0.3 | 0.2 | | 3-18 hrs |
| IJ5-179 | 0.01 | 0.02 | | | | 0.4 | 3-18 hrs |

175 > 172 > 176 > 170, 174 (177, 178, 179)
170 vs. 176: increasing DBU boost speed of gelation;
172 vs. 176: increasing TEA also boosts speed of gelation;
172 vs. 174: Excessive of TCDCDA decrease speed of gelation
173 vs. 178: Increasing TEA boosts speed of gelation,
171 vs. 175: SR 295 gelation fast than TCDCDA
173 vs. 175: somewhere between 0.3% and 0.4% of DBU change the speed of gelation dramatically.

TABLE 2

Compositions and Viscosities of Formulated Base Resins for Viscosity-increasing

| Resin Compositions | PETMP %, wt/wt | ETTMP %, wt/wt | TPH Resin %, wt/wt | IsosorbideR %, wt/wt | SDR %, wt/wt | UDMA %, wt/wt | EBPADMA %, wt/wt | Inhibitors %, wt/wt | TEGDMA %, wt/wt | Viscosity @20° C. Pa·s |
|---|---|---|---|---|---|---|---|---|---|---|
| IJ5-184 | 20 | | 80 | | | | | | | 9-17 |
| IJ5-188 | | | | | | | | | | |
| IJ5-192 | | | | | | | | | | |
| IJ5-208 | | | | | | | | | | |
| IJ6-030 | | | | | | | | | | |
| IJ6-055 | | | | | | | | | | |
| IJ5-204 | 20 | | | 80 | | | | | | gelled |
| IJ5-206 | 20 | | | | 80 | | | | | gelled |
| IJ6-009 | 20 | | | | | 80 | | | | 10 |
| IJ6-008 | 20 | | | | | | 80 | | | 2 |
| IJ6-036 | | | | | | | | | | |
| IJ6-055 | | | | | | | | | | |
| IJ6-073 | | | | | | | | | | |
| IJ6-087 | | | | | | | | | | |
| IJ6-106 | | | | | | | | | | |
| IJ6-113 | | | | | | | | | | |
| IJ6-151 | | | | | | | | | | |
| IJ6-188 | | | | | | | | | | |
| IJ6-020 | 20 | | 80 | | | | | PYG/1.00 | | |
| IJ6-021 | 20 | | | | 70 | | | PYG/1.00 | 10 | |
| IJ6-022 | 20 | | 80 | | | | | TTBPP/1.00 | | |
| IJ6-023 | 20 | | | | 70 | | | TTBPP/1.00 | 10 | |
| IJ6-024 | 20 | | 80 | | | | | TPP/1.00 | | |
| IJ6-025 | 20 | | | | 70 | | | TPP/1.00 | 10 | |
| IJ6-026 | 20 | | 80 | | | | | L-Gallate/1.00 | | |
| IJ6-027 | 20 | | | | 70 | | | L-Gallate/1.00 | 10 | |
| IJ6-030 | 20 | | 80 | | | | | | | |
| IJ6-032 | 20 | | | | 70 | | | | 10 | |
| IJ6-034 | 20 | | | 70 | | | | | 10 | |

TABLE 2-continued

Compositions and Viscosities of Formulated Base Resins for Viscosity-increasing

| Resin Compositions | PETMP %, wt/wt | ETTMP %, wt/wt | TPH Resin %, wt/wt | IsosorbideR %, wt/wt | SDR %, wt/wt | UDMA %, wt/wt | EBPADMA %, wt/wt | Inhibitors %, wt/wt | TEGDMA %, wt/wt | Viscosity @20° C. Pa · s |
|---|---|---|---|---|---|---|---|---|---|---|
| IJ6-036 | 20 | | | | | | 80 | | | 2 |
| IJ6-047 | | 20 | 80 | | | | | | | 5 |
| IJ7-009 | 30 | | | | | | 70 | | | |
| IJ7-010 | 25 | | | | | | 75 | | | |
| IJ7-047 | 33 | | | | | | 67 | | | |
| IJ7-059 | 40 | | | | | | 60 | | | |
| IJ7-071 | | | | | | | | | | |
| IJ7-060 | 50 | | | | | | 50 | | | |

PYG: Pyrogallol
TTBPP: Tris(2,4,-di(tert)-butylpheyl0phosphite
TPP: Triphenyl phosphite
L-Gallate: Lauryl gallate

TABLE 3

Compositions and Viscosities of Formulated Catalyst Resins for Viscosity-increasing

| Resin Compositions | TPH Resin %, wt/wt | CN2303 %, wt/wt | SR295 %, wt/wt | TCDCDA %, wt/wt | CQ %, wt/wt | BHT %, wt/wt | LTPO %, wt/wt | DBU %, wt/wt | TEA %, wt/wt | Viscosity @20° C. Pa · s |
|---|---|---|---|---|---|---|---|---|---|---|
| IJ5-185 | 50 | | | 50 | 0.31 | 0.03 | 0.80 | 0.28 | | 2 |
| IJ5-189 | 50 | | | 50 | | | | 0.21 | 0.14 | 2 |
| IJ5-193 | 70 | | 30 | | 0.31 | 0.03 | 0.80 | 0.56 | | 9 |
| IJ5-194 | 70 | | 30 | | 0.31 | 0.03 | 0.80 | 0.42 | 0.28 | 9 |
| IJ6-051 | 50 | 50 | | | 0.31 | 0.03 | 0.80 | 0.56 | | 2 |
| IJ6-052 | 50 | 50 | | | 0.31 | 0.03 | 0.80 | 0.56 | | 5 |

| Resin Compositions | EBPADAM %, wt/wt | CN2303 %, wt/wt | IsosorbideR %, wt/wt | TCDCDA %, wt/wt | CQ %, wt/wt | BHT %, wt/wt | LTPO %, wt/wt | DBU %, wt/wt | TEA %, wt/wt | Viscosity @20° C. Pa · s |
|---|---|---|---|---|---|---|---|---|---|---|
| IJ6-053 | 50 | 50 | | | 0.31 | 0.03 | 0.80 | 0.56 | | 1 |
| IJ6-054 | | 50 | 50 | | 0.31 | 0.03 | 0.80 | 0.42 | 0.28 | 4 |
| IJ6-070 | 50 | | | 50 | 0.31 | 0.03 | 0.80 | 0.56 | | 6 |
| IJ6-084 | 50 | | | 50 | 0.31 | 0.03 | 0.80 | 0.84 | | 22 |

| Resin Compositions | EBPADAM %, wt/wt | SR295 %, wt/wt | TPH Resin %, wt/wt | TCDCDA %, wt/wt | CQ %, wt/wt | BHT %, wt/wt | LTPO %, wt/wt | DBU %, wt/wt | SDR %, wt/wt | Viscosity @20° C. Pa · s |
|---|---|---|---|---|---|---|---|---|---|---|
| IJ6-071 | 50 | 50 | | | 0.31 | 0.03 | 0.80 | 0.56 | | 1 |
| IJ6-085 | 50 | 50 | | | 0.31 | 0.03 | 0.80 | 0.84 | | 2 |
| IJ6-072 | | 50 | 50 | | 0.31 | 0.03 | 0.80 | 0.56 | | 2 |
| IJ6-069 | | | 50 | 50 | 0.31 | 0.03 | 0.80 | 0.56 | | 2 |
| IJ6-070 | | | | | | | | | | |
| IJ6-083 | | | 50 | 50 | 0.31 | 0.03 | 0.80 | 0.84 | | 5 |
| IJ6-084 | | | | | | | | | | |
| IJ6-086 | | 50 | 50 | | 0.31 | 0.03 | 0.80 | 0.84 | | 18 |
| IJ6-097 | | | 50 | 50 | 0.31 | 0.03 | 0.80 | 1.12 | | 2 |
| IJ6-098 | | | | 50 | 0.31 | 0.03 | 0.80 | 1.12 | 50 | 2 |
| IJ6-099 | 50 | | | 50 | 0.31 | 0.03 | 0.80 | 1.12 | | 2 |
| IJ6-114 | 50 | 50 | | | 0.31 | 0.03 | 0.80 | 1.12 | | 2 |
| IJ6-147 | | 50 | 50 | | 0.31 | 0.03 | 0.80 | 0.86 | | 2 |
| IJ6-148 | 50 | 50 | | | 0.31 | 0.03 | 0.80 | 0.86 | | 2 |
| IJ6-149 | | 50 | 50 | | 0.31 | 0.03 | 0.80 | 0.86 | EDAB 0.40 | 2 |
| IJ6-150 | 50 | 50 | | | 0.31 | 0.03 | 0.80 | 0.86 | EDAB 0.40 | 2 |
| IJ7-007 | | 35 | 65 | | 0.31 | | 0.80 | 0.75 | EDAB 0.40 | NA |
| IJ7-008 | | 35 | 65 | | 0.31 | | 0.80 | 0.75 | | NA |
| IJ7-046 | | 25 | 75 | | 0.31 | 0.03 | 0.80 | 0.86 | EDAB 0.40 | NA |
| IJ7-058 | | 35 | 65 | | 0.31 | 0.03 | 0.80 | 0.86 | EDAB 0.40 | NA |
| IJ7-070 | | 35 | 65 | | 0.31 | 0.03 | 0.80 | 0.86 | EDAB 0.40 | NA |

TABLE 3-continued

Compositions and Viscosities of Formulated Catalyst Resins for Viscosity-increasing

| Resin Compositions | SR295 %, wt/wt | TCDCDA %, wt/wt | IsosorbideR %, wt/wt | SDR %, wt/wt | CQ %, wt/wt | BHT %, wt/wt | LTPO %, wt/wt | DBU %, wt/wt | TEA %, wt/wt | Viscosity @20° C. Pa · s |
|---|---|---|---|---|---|---|---|---|---|---|
| IJ5-205 | 30 | | 70 | | 0.31 | 0.03 | 0.80 | 0.42 | 0.28 | 35 |
| IJ5-207 | 30 | | | 70 | 0.163 | 0.03 | 0.80 | 0.42 | 0.28 | 52 |
| IJ6-028 | 50 | 50 | | | 0.31 | 0.03 | 0.80 | 0.07 | | 2 |
| IJ6-100 | | 50 | 50 | | 0.31 | 0.03 | 0.80 | 1.12 | | 2 |

Further the flowability of such formulated composition would also vary depending upon the filler and filler content. As showed in Table 2, a variety of flowable compositions with 55-60% wt/wt of fillers was readily formulated by variable DBU contents and different acrylate resins (TD-CDDA and SD 295) and different methacrylate resins (TPH resin, SDR resin and Isosorbide Resin). It was also concluded that higher concentration of DBU is more effective than DBU/TEA mixture; and SR295 is more effective than TCDCDA in term of promoting stage one network formation.

Furthermore, as showed in Table 4 and 5, excellent mechanical propertied, flexural strength of 136-152 MPa and flexural modulus of 6750-8200M, could be achieved from such two-stage cure/viscosity-increasing systems. In addition, lower polymerization stress of 2.3-2.8 MP vs. 3.3 MPa were also resulted from such two-stage cure process. Further lower polymerization stress of 2.07 MPa was found upon 90 min delayed light curing process, which indirectly confirmed the stage-one network formation process proceeded. In addition, it was also noted DBU could also act as accelerator for CQ/LTPO photopolymerization as evident by the effective curing under a single-band LED irradiation (IQ2 LED).

It was surprisingly found that both two urethane-based methacrylate resins (isosorbide-based resin and SDR resin) are not chemically compatible with PETMP, as evident by the gelation of IJ5-204 and IJ5-206, respectively. There is no any catalyst presented in these systems and they are all methacrylate resins. Thus it is speculated somehow the impurity in either isosorbide resin or SDR resin can significantly destabilize such thiol-ene system of polythiol (PETMP) and methacrylates. However, the better stability demonstrated by other urethane-based resin (TPH resin) might suggest that there is no (or less) such "impurity" in TPH resin. Indeed a slow viscosity increasing in TPH resin/PETMP was eventually demonstrated they follow similar trend of instability after it was aged over night at RT though no gel was formed as showed by the viscosity of 17 Pa·s of IJ5-192 vs. 9 Pa·s for those freshly mixed resin blends, IJ5-184, IJ5-188 and IJ5-208. In addition, if freshly mixed isosorbide resin/PETMP or SDR resin/PETMP were immediately formulated into composites (IJ6-001 or IJ6-003 in Table 2), their stability got improved but they still tended to get stiff, which indicated a slower gelation process occurred within the pastes then resin blends.

TABLE 4

Compositions and Properties of Formulated Flowables for Viscosity-increasing

| Dual Paste | Paste Compositions | | Stress @ 60 min (QHLBlue) | Halogen Light Compr. t. (Mpa) | Halogen Light Flex. St. (Mpa) |
|---|---|---|---|---|---|
| | Base Paste | Catalyst Paste | MPa | Compr.Mod. (Mpa) | Flex. Mod.(Mpa) |
| IJ5-186 | Resin/IJ5-184 40.05% Filler/XJ8-148 59.95% | | 2.83 2.73 (w/ 1 min delayed) 2.61 | 367 ± 26 4420 ± 300 | 145 ± 11 7880 ± 600 |
| IJ5-187 | | Resin/IJ5-185 41.65% Filler/XJ8-148 58.35% | (w/ 90 min delayed) | | |
| IJ5-190 | Resin/IJ5-188 39.95% Filler/XJ8-148 60.05% | | 2.81 2.88 (w/ 1 min delayed) 2.07 | 342 ± 45 4120 ± 40 | 152 ± 15 8190 ± 470 |
| IJ5-191 | | Resin/IJ5-189 44.40% Filler/XJ8-148 55.60% | (w/ 90 min delayed) | | |
| IJ5-195 | Resin/IJ5-192 45.01% Filler/XJ8-148 54.99% | | 2.31 | 317 ± 28 3990 ± 370 | 136 ± 7 6750 ± 460 |
| IJ5-196 | | Resin/IJ5-193 41.65% Filler/XJ8-148 58.35% | | | |
| IJ5-195 | Resin/IJ5-192 45.01% Filler/XJ8-148 54.99% | | 2.45 | 333 ± 12 4360 ± 60 | 129 ± 4 6700 ± 400 |

TABLE 4-continued

Compositions and Properties of Formulated Flowables for Viscosity-increasing

| Dual Paste | Paste Compositions | | Stress @ 60 min (QHLBlue) | Halogen Light Compr. t. (Mpa) | Halogen Light Flex. St. (Mpa) |
| --- | --- | --- | --- | --- | --- |
| | Base Paste | Catalyst Paste | MPa | Compr.Mod. (Mpa) | Flex. Mod.(Mpa |
| IJ5-197 | | Resin/IJ5-194 45.03% Filler/XJ8-148 54.97% | | | |
| IJ6-005 | Resin/IJ5-208 45.00% Filler/XJ8-148 55.00% | | 2.26 2.76 (w/ 30 min delayed) | 348 ± 18 3680 ± 320 | 143 ± 8 6780 ± 480 |
| IJ6-002 | | Resin/IJ5-205 45.00% Filler/XJ8-148 55.00% | | | |
| IJ6-005 | Resin/IJ6-028 45.00% Filler/XJ8-148 55.00% | | 2.59 2.06 (w/ 60 min delayed) | 386 ± 29 3000 ± 270 | 140 ± 7 7140 ± 130 |
| IJ6-029 | | Resin/IJ6-030 45.00% Filler/XJ8-148 55.00% | | | |
| IJ6-029 | Resin/IJ5-208 45.00% Filler/XJ8-148 55.00% | | 2.21 2.34 (w/ 60 min delayed) | 380 ± 12 3680 ± 320 | 132 ± 12 6550 ± 650 |
| IJ6-037 | | Resin/IJ6-036 45.00% Filler/XJ8-148 55.00% | | | |
| IJ6-029 | Resin/IJ5-208 45.00% Filler/XJ8-148 55.00% | | NA | 274 ± 27 2670 ± 260 | 126 ± 15 6350 ± 640 |
| IJ6-048 | | Resin/IJ6-047 45.00% Filler/XJ8-148 55.00% | | | |
| IJ6-060 | Resin/IJ6-055 45.00% Filler/XJ8-148 55.00% | | 2.62 2.64 (w/ 60 min delayed) | 274 ± 24 3370 ± 280 | 98 ± 7 4950 ± 360 |
| IJ6-056 | | Resin/IJ6-051 45.00% Filler/XJ8-148 55.00% | | | |
| IJ6-060 | Resin/IJ6-55 45.00% Filler/XJ8-148 55.00% | | 2.56 2.15 (w/ 60 min delayed) | 343 ± 30 3690 ± 200 | 106 ± 9 4750 ± 280 |
| IJ6-057 | | Resin/IJ6-052 45.00% Filler/XJ8-148 55.00% | | | |
| IJ6-060 | Resin/IJ6-055 45.00% Filler/XJ8-148 55.00% | | 2.41 2.09 (w/ 60 min delayed) | 320 ± 35 3630 ± 380 | 116 ± 4 5280 ± 510 |
| IJ6-058 | | Resin/IJ6-053 45.00% Filler/XJ8-148 55.00% | | | |
| IJ6-060 | Resin/IJ6-73 45.00% Filler/XJ8-148 55.00% | | 2.20 2.15 (w/ 60 min delayed) | 330 ± 30 3590 ± 220 | 112 ± 4 5450 ± 60 |
| IJ6-059 | | Resin/IJ6-069 45.00% Filler/XJ8-148 55.00% | | | |
| IJ6-080 | Resin/IJ6-73 45.00% Filler/XJ8-148 55.00% | | 2.62 2.64 (w/ 60 min delayed) | 261 ± 20 3950 ± 210 | 123 ± 12 5890 ± 280 |

TABLE 4-continued

Compositions and Properties of Formulated Flowables for Viscosity-increasing

| Dual Paste | Paste Compositions | | Stress @ 60 min (QHLBlue) | Halogen Light Compr. t. (Mpa) | Halogen Light Flex. St. (Mpa) |
|---|---|---|---|---|---|
| | Base Paste | Catalyst Paste | MPa | Compr.Mod. (Mpa) | Flex. Mod.(Mpa |
| IJ6-074 | | Resin/IJ6-069 45.00% Filler/XJ8-148 55.00% | | | |
| IJ6-092 | Resin/IJ6-87 45.00% Filler/XJ8-148 55.00% | | 2.21 2.34 (w/ 60 min delayed) | 230 ± 25 3470 ± 100 | 124 ± 9 6000 ± 300 |
| IJ6-088 | | Resin/IJ6-083 45.00% Filler/XJ8-148 55.00% | | | |
| IJ6-080 | Resin/IJ6-73 45.00% Filler/XJ8-148 55.00% | | 2.56 2.15 (w/ 60 min delayed) | 260 ± 30 4100 ± 1600 | 128 ± 13 6450 ± 180 |
| IJ6-075 | | Resin/IJ6-070 45.00% Filler/XJ8-148 55.00% | | | |
| IJ6-092 | Resin/IJ6-87 45.00% Filler/XJ8-148 55.00% | | 2.60 2.00 (w/ 60 min delayed) | 308 ± 35 3620 ± 330 | 117 ± 8 5070 ± 200 |
| IJ6-089 | | Resin/IJ6-084 45.00% Filler/XJ8-148 55.00% | | | |
| IJ6-080 | Resin/IJ6-73 45.00% Filler/XJ8-148 55.00% | | 2.41 2.09 (w/ 60 min delayed) | 299 ± 30 4180 ± 250 | 135 ± 8 6250 ± 210 |
| IJ6-076 | | Resin/IJ6-071 45.00% Filler/XJ8-148 55.00% | | | |
| IJ6-092 | Resin/IJ6-87 45.00% Filler/XJ8-148 55.00% | | 2.86 2.29 (w/ 60 min delayed) | 277 ± 25 3810 ± 240 | 119 ± 9 4950 ± 480 |
| IJ6-090 | | Resin/IJ6-085 45.00% Filler/XJ8-148 55.00% | | | |
| IJ6-080 | Resin/IJ6-73 45.00% Filler/XJ8-148 55.00% | | 2.37 2.15 (w/ 60 min delayed) | 266 ± 20 3860 ± 100 | 142 ± 6 6330 ± 120 |
| IJ6-077 | | Resin/IJ6-072 45.00% Filler/XJ8-148 55.00% | | | |
| IJ6-092 | Resin/IJ6-87 45.00% Filler/XJ8-148 55.00% | | 3.00 1.58 (w/ 60 min delayed) | 280 ± 25 3770 ± 230 | 120 ± 4 5300 ± 280 |
| IJ6-091 | | Resin/IJ6-086 45.00% Filler/XJ8-148 55.00% | | | |
| IJ6-112 | Resin/IJ6-106 40.00% Filler/XJ8-148 60.00% | | 2.60 2.46 (w/ 60 min delayed) | 206 ± 20 4000 ± 170 | 123 ± 9 7000 ± 760 |
| IJ6-108 | | Resin/IJ6-097 40.00% Filler/XJ8-148 60.00% | | | |
| IJ6-112 | Resin/IJ6-106 40.00% Filler/XJ8-148 60.00% | | 2.07 2.39 (w/ 60 min delayed) | 230 ± 23 3200 ± 140 | 125 ± 14 6640 ± 250 |

TABLE 4-continued

Compositions and Properties of Formulated Flowables for Viscosity-increasing

| Dual Paste | Paste Compositions | | Stress @ 60 min (QHLBlue) MPa | Halogen Light Compr. t. (Mpa) Compr.Mod. (Mpa) | Halogen Light Flex. St. (Mpa) Flex. Mod.(Mpa |
|---|---|---|---|---|---|
| | Base Paste | Catalyst Paste | | | |
| IJ6-109 | | Resin/IJ6-098 40.00% Filler/XJ8-148 60.00% | | | |
| IJ6-112 | Resin/IJ6-106 40.00% Filler/XJ8-148 60.00% | | 2.02 2.06 (w/ 60 min delayed) | 228 ± 15 3550 ± 420 | 118 ± 12 6900 ± 370 |
| IJ6-110 | | Resin/IJ6-099 40.00% Filler/XJ8-148 60.00% | | | |
| IJ6-112 | Resin/IJ6-106 40.00% Filler/XJ8-148 60.00% | | 2.16 1.72 (w/ 60 min delayed) | 230 ± 20 3550 ± 560 | 132 ± 3 6960 ± 200 |
| IJ6-111 | | Resin/IJ6-100 40.00% Filler/XJ8-148 60.00% | | | |
| IJ6-115 | Resin/IJ6-113 40.00% Filler/XJ8-148 60.00% | | 2.36 2.37 (w/ 60 min delayed) | 270 ± 30 3750 ± 60 | 100 ± 10 4900 ± 450 |
| IJ6-116 | | Resin/IJ6-114 40.00% Filler/XJ8-148 60.00% | | | |
| IJ6-117 | Resin/IJ6-113 40.00% Filler/XJ8-148 60.00% | | 2.32 2.36 (w/ 60 min delayed) | 195 ± 30 3960 ± 400 | 79 ± 7 5170 ± 560 |
| IJ6-118 | | Resin/IJ6-114 40.00% Filler/XJ8-148 60.00% | | | |
| IJ6-115 | Resin/IJ6-113 40.00% Filler/XJ8-148 60.00% | | 2.36 2.37 (w/ 60 min delayed) | 270 ± 30 3750 ± 60 | 100 ± 10 4900 ± 450 |
| IJ6-116 | | Resin/IJ6-114 40.00% Filler/XJ8-148 60.00% | | | |
| IJ6-117 | Resin/IJ6-113 40.00% Filler/XJ8-148 60.00% | | 2.32 2.36 (w/ 60 min delayed) | 195 ± 30 3960 ± 400 | 79 ± 7 5170 ± 560 |
| IJ6-118 | | Resin/IJ6-114 40.00% Filler/XJ8-148 60.00% | | | |

TABLE 5

Compositions and Properties of Formulated Flowables for Viscosity-increasing

| Mixing Methods | Dual Pastes | Paste Composition | | Stress @ 60 min (QHLBlue) MPa | Halogen Light Compr. t.(Mpa) Compr. Mod.(Mpa) | Halogen Light Flex. St.(Mpa) Flex. Mod.(Mpa |
|---|---|---|---|---|---|---|
| | | Base Paste | Catalyst Paste | | | |
| SpeedMix | IJ6-115 | Resin/IJ6-113 40.00% Filler/XJ8-148 60.00% | | 2.36 2.37 (w/30 min delayed) | 270 ± 30 3750 ± 60 | 100 ± 10 4900 ± 450 |

TABLE 5-continued

Compositions and Properties of Formulated Flowables for Viscosity-increasing

| Mixing Methods | Dual Pastes | Paste Composition Base Paste | Paste Composition Catalyst Paste | Stress @ 60 min (QHLBlue) MPa | Halogen Light Compr. t.(Mpa) Compr. Mod.(Mpa) | Halogen Light Flex. St.(Mpa) Flex. Mod.(Mpa |
|---|---|---|---|---|---|---|
| | IJ6-116 | | Resin/IJ6-114 40.00% Filler/XJ8-148 60.00% | | | |
| SpeedMix | IJ6-117 | Resin/IJ6-113 40.00% Filler/XJ8-148 60.00% | | 2.32 2.36 (w/30 min delayed) | 195 ± 30 3960 ± 400 | 79 ± 7 5170 ± 560 |
| | IJ6-118 | | Resin/IJ6-114 40.00% Filler/XJ8-148 60.00% | | | |
| Resodyn | IJ6-139 | Resin/IJ6-113 40.00% Filler/XJ8-148 60.00% | | 2.90 2.51 (w/30 min delayed) | 330 ± 20 3930 ± 340 | 122 ± 5 5110 ± 300 |
| | IJ6-140 | | Resin/IJ6-114 40.00% Filler/XJ8-148 60.00% | | | |
| Resodyn | IJ6-141 | Resin/IJ6-113 40.00% Filler/XJ8-148 60.00% | | 2.78 2.32 (w/30 min delayed) | 277 ± 20 4350 ± 160 | 104 ± 10 5440 ± 420 |
| | IJ6-142 | | Resin/IJ6-114 40.00% Filler/XJ8-148 60.00% | | | |
| RossMixer | IJ6-152 | Resin/IJ6-147 40.00% Filler/XJ8-148 60.00% | | 3.50 2.94 (w/30 min delayed) | 295 ± 10 3800 ± 130 | 123 ± 12 6570 ± 380 |
| | IJ6-156 | | Resin/IJ6-151 40.00% Filler/XJ8-148 60.00% | | | |
| RossMixer | IJ6-153 | Resin/IJ6-148 40.00% Filler/XJ8-148 60.00% | | 3.25 2.72 (w/30 min delayed) | 307 ± 10 3520 ± 180 | 122 ± 9 6910 ± 190 |
| | IJ6-156 | | Resin/IJ6-151 40.00% Filler/XJ8-148 60.00% | | | |
| RossMixer | IJ6-154 | Resin/IJ6-149 40.00% Filler/XJ8-148 60.00% | | 3.65 2.88 (w/30 min delayed) | 300 ± 20 3780 ± 250 | 130 ± 7 6910 ± 400 |
| | IJ6-156 | | Resin/IJ6-151 40.00% Filler/XJ8-148 60.00% | | | |
| RossMixer | IJ6-155 | Resin/IJ6-150 40.00% Filler/XJ8-148 60.00% | | 3.10 3.47 (w/30 min delayed) | 300 ± 30 3800 ± 450 | 116 ± 6 5950 ± 250 |
| | IJ6-156 | | Resin/IJ6-151 40.00% Filler/XJ8-148 60.00% | | | |
| Resodyn | IJ6-158 | Resin/IJ6-147 40.00% Filler/XJ8-148 60.00% | | 2.90 3.33 (w/30 min delayed) | 294 ± 30 3870 ± 270 | 116 ± 6 6080 ± 450 |
| | IJ6-162 | | Resin/IJ6-151 40.00% Filler/XJ8-148 60.00% | | | |

TABLE 5-continued

Compositions and Properties of Formulated Flowables for Viscosity-increasing

| Mixing Methods | Dual Pastes | Paste Composition Base Paste | Catalyst Paste | Stress @ 60 min (QHLBlue) MPa | Halogen Light Compr. t.(Mpa) Compr. Mod.(Mpa) | Halogen Light Flex. St.(Mpa) Flex. Mod.(Mpa |
|---|---|---|---|---|---|---|
| Resodyn | IJ6-159 | Resin/IJ6-148 40.00% Filler/XJ8-148 60.00% | | 2.78 3.20 (w/30 min delayed) | 272 ± 20 3730 ± 140 | 126 ± 4 5610 ± 400 |
| | IJ6-162 | | Resin/IJ6-151 40.00% Filler/XJ8-148 60.00% | | | |
| Resodyn | IJ6-160 | Resin/IJ6-149 40.00% Filler/XJ8-148 60.00% | | 3.84 3.06 (w/30 min delayed) | 286 ± 20 3560 ± 310 | 121 ± 7 6230 ± 210 |
| | IJ6-162 | | Resin/IJ6-151 40.00% Filler/XJ8-148 60.00% | | | |
| Resodyn | IJ6-161 | Resin/IJ6-150 40.00% Filler/XJ8-148 60.00% | | 3.25 2.98 (w/30 min delayed) | 289 ± 15 3450 ± 300 | 126 ± 4 5970 ± 410 |
| | IJ6-162 | | Resin/IJ6-151 40.00% Filler/XJ8-148 60.00% | | | |
| Resodyn | IJ7-012 | Resin/IJ7-007 35.00% Filler/XJ8-148 65.00% | | 3.06 2.83 (w/30 min delayed) | 273 ± 20 4210 ± 210 | 141 ± 4 7570 ± 160 |
| | IJ7-016 | | Resin/IJ7-009 35.00% Filler/XJ8-148 65.00% | | | |
| Resodyn | IJ7-013 | Resin/IJ7-008 35.00% Filler/XJ8-148 65.00% | | 2.53 2.93 (w/30 min delayed) | 253 ± 20 3470 ± 230 | 135 ± 9 7530 ± 250 |
| | IJ7-016 | | Resin/IJ7-009 35.00% Filler/XJ8-148 65.00% | | | |
| Resodyn | IJ7-014 | Resin/IJ7-007 35.00% Filler/XJ8-148 65.00% | | 3.01 2.69 (w/30 min delayed) | 252 ± 20 3270 ± 200 | 132 ± 6 7470 ± 270 |
| | IJ7-017 | | Resin/IJ7-010 35.00% Filler/XJ8-148 75.00% | | | |
| Resodyn | IJ7-015 | Resin/IJ7-008 35.00% Filler/XJ8-148 65.00% | | 2.83 2.49 (w/30 min delayed) | 255 ± 20 4320 ± 290 | 123 ± 8 7600 ± 410 |
| | IJ7-017 | | Resin/IJ7-010 35.00% Filler/XJ8-148 65.00% | | | |
| Resodyn | IJ7-050 | Resin/IJ7-046 35.00% Filler/XJ8-148 65.00% | | 2.66 2.46 (w/30 min delayed) | 270 ± 18 3950 ± 350 | 128 ± 9 7170 ± 350 |
| | IJ7-051 | | Resin/IJ7-047 35.00% Filler/XJ8-148 75.00% | | | |
| Resodyn | IJ7-062A | Resin/IJ7-058 35.00% Filler/XJ8-148 65.00% | | 2.82 2.37 (w/30 min delayed) | 258 ± 14 3260 ± 180 | 118 ± 4 6170 ± 270 |
| | IJ7-063 | | Resin/IJ7-059 35.00% Filler/XJ8-148 65.00% | | | |

TABLE 5-continued

Compositions and Properties of Formulated Flowables for Viscosity-increasing

| Mixing Methods | Dual Pastes | Paste Composition | | Stress @ 60 min (QHLBlue) MPa | Halogen Light Compr. t.(Mpa) Compr. Mod.(Mpa) | Halogen Light Flex. St.(Mpa) Flex. Mod.(Mpa |
| --- | --- | --- | --- | --- | --- | --- |
| | | Base Paste | Catalyst Paste | | | |
| Resodyn | IJ7-062B | Resin/IJ7-046 35.00% Filler/XJ8-148 65.00% | | 2.95 2.25 (w/30 min delayed) | 242 ± 27 2800 ± 410 | 109 ± 4 6100 ± 380 |
| | IJ7-064 | | Resin/IJ7-060 35.00% Filler/XJ8-148 65.00% | | | |

TABLE 6

Compositions and Properties of Formulated Flowables for Viscosity-increasing

| Composite Compositions | IJ6-005 | IJ6-001 | IJ6-003 |
| --- | --- | --- | --- |
| Resin Blend | IJ5-208 45.01% Mol % Thiol: 0.0737 | IJ5-204* 45.01% Mol % Thiol: 0.0737 | IJ5-206* 45.03% Mol % Thiol: 0.0737 |
| Filler Blend (XJ8-148) | 907445(57) 907446(29) 999141(14) 54.99% | 907445(57) 907446(29) 999141(14) 54.99% | 907445(57) 907446(29) 999141(14) 54.97% |
| Paste Appearance | No gel | soft gel | stiff gel |

Figure 9:
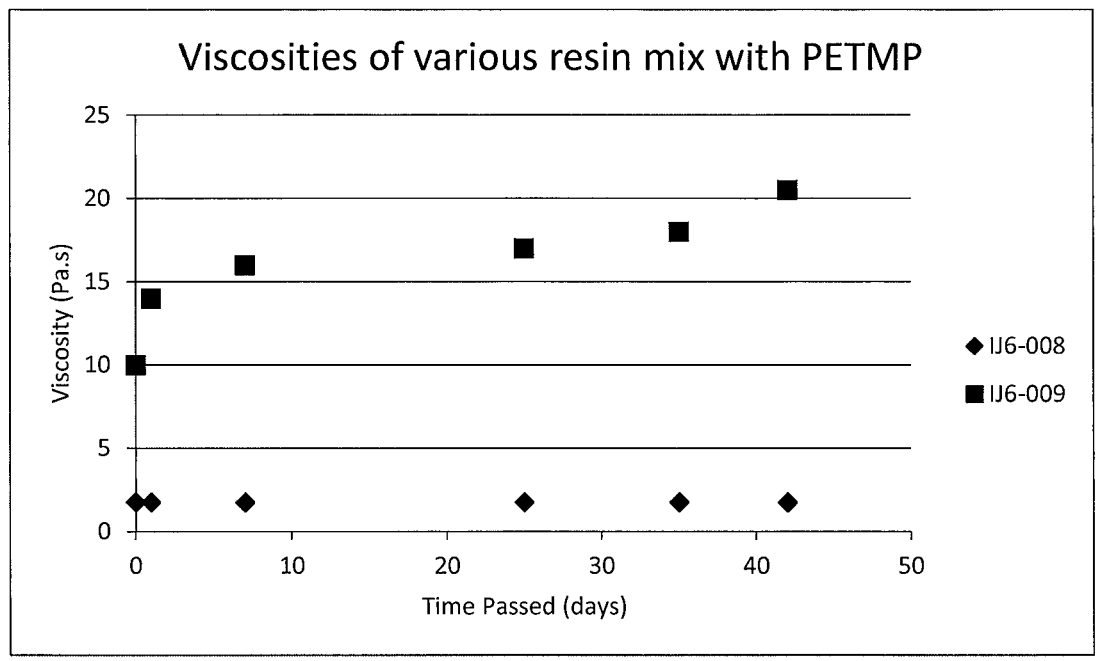
FIG. 9 shows the aging effect on viscosity of various mixed resin systems.

*freshly mixed resin blend for immediate use in paste-making;

Consequently, it was discovered that a remarkably stable pair of methacrylated resin and polythiol (PETMP) could be achieved from EBPADMA during the extensive resin screening study for improved resin stability: no any viscosity increase as measured after 42 days/RT aging (see FIG. 9), in comparison to 10-20 fold of increase in viscosity for the other resin like TPH resin. It was also found UDMA demonstrated better compatibility with PETMP even though there was slight increase (doubled) in viscosity.

Figure 10:
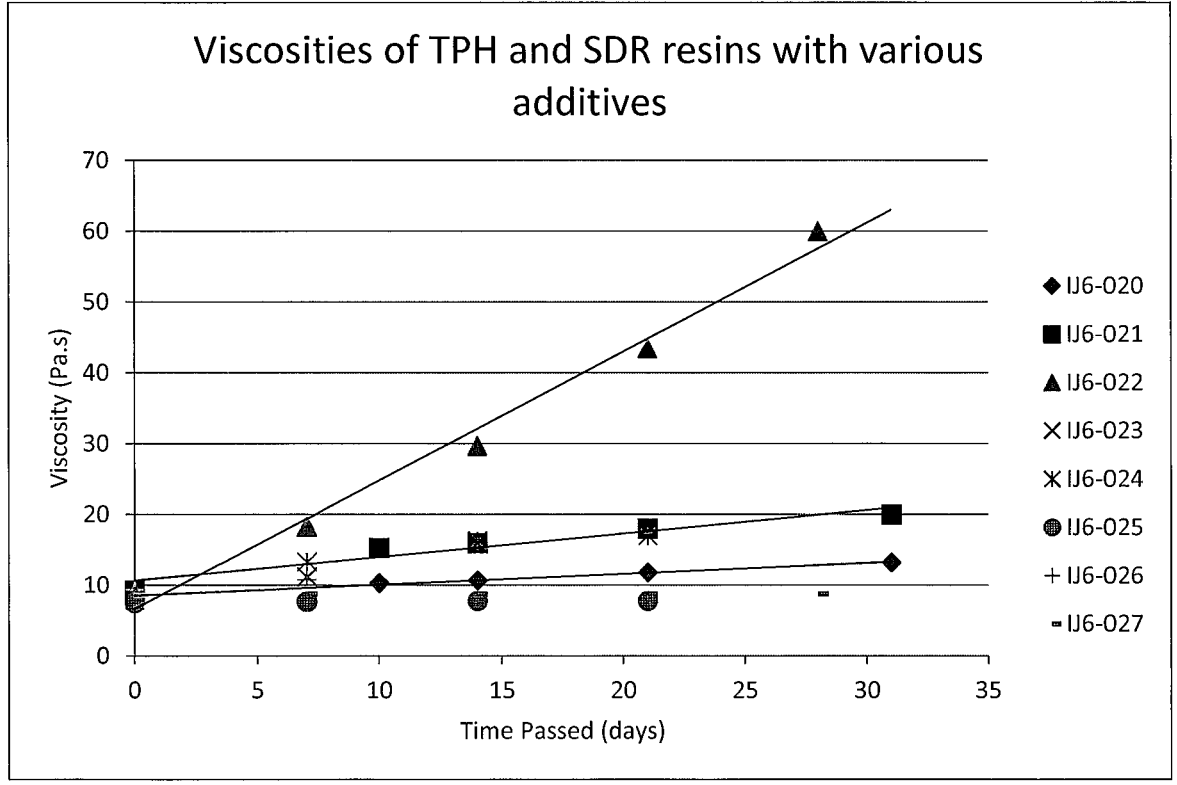
FIG. 10 shows the viscosity of TPH® and SDR® resins with various additives.
Figure 11:
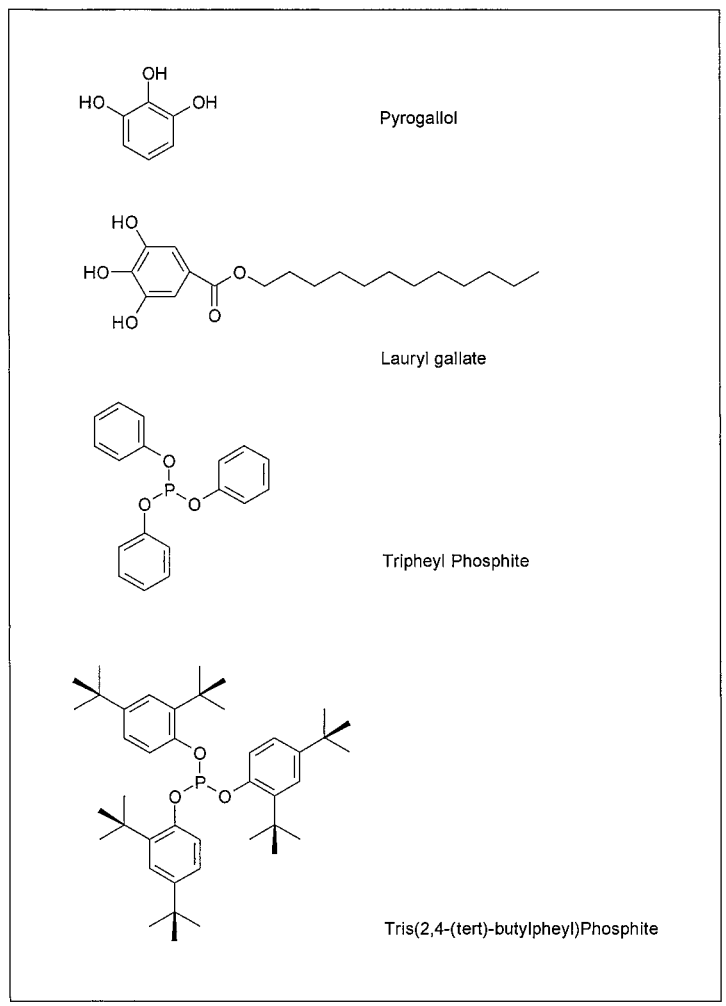
FIG. 11 is a schematic of molecular structures of thiol inhibitors.
Figure 12:
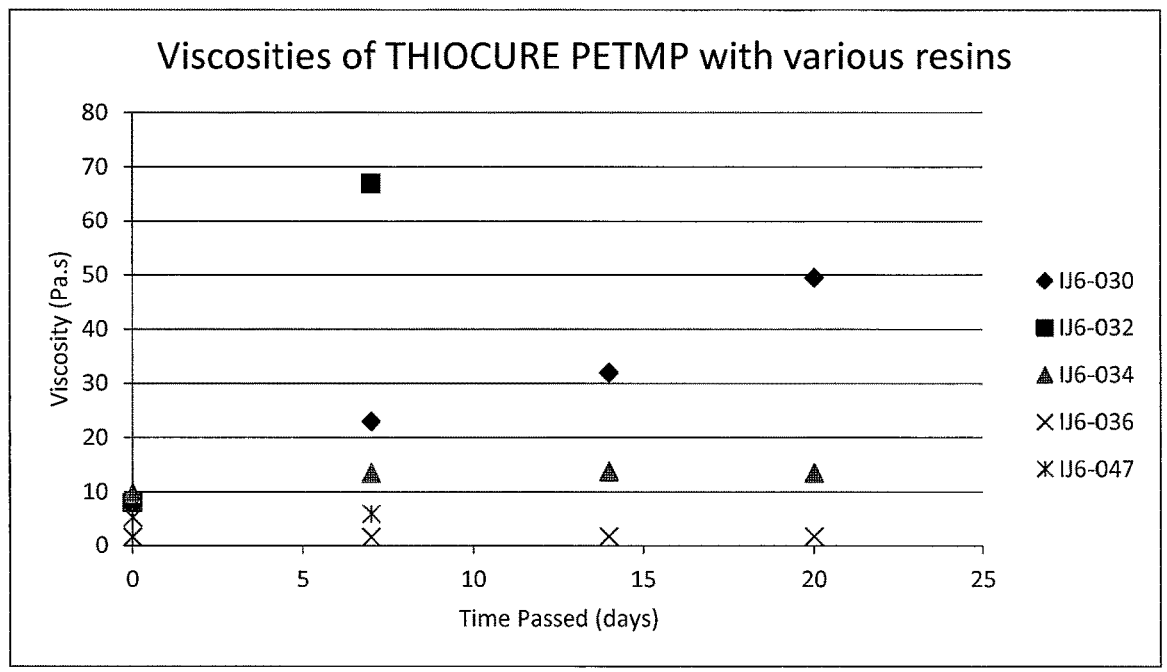
FIG. 12 shows the aging effect on viscosity of THIOCURE PETMP with various resins.

Other approach to stabilize polythiol/methacrylated resin system was also examined in TPH resin and SDR resin, respectively, see FIGS. 10 and 11. The inhibitors included PYG, TTBPP, TPP and L-Gallate (Table 2). They were loaded in the resin blend in 1% wt/wt. The preliminary results revealed that the effectiveness of these inhibitors was varied depending upon the methacrylated resin, like TPH resin or SDR resin. PYG appears more effective in inhibiting the viscosity increase in TPH resin system than in SDR resin but discoloration occurred in both resin systems. TTBPP would not work at all in both TPH resin and SDR resin. However, TPP appears working better in SDR resin than in TPH resin; L-Gallate does not work with TPH resin but worked very well in SDR resin system. Therefore both TPP and L-Gallate should be considered as effective additives for SDR resin/PETMP system and none of them worked for TPH resin, unfortunately.

Figure 13:
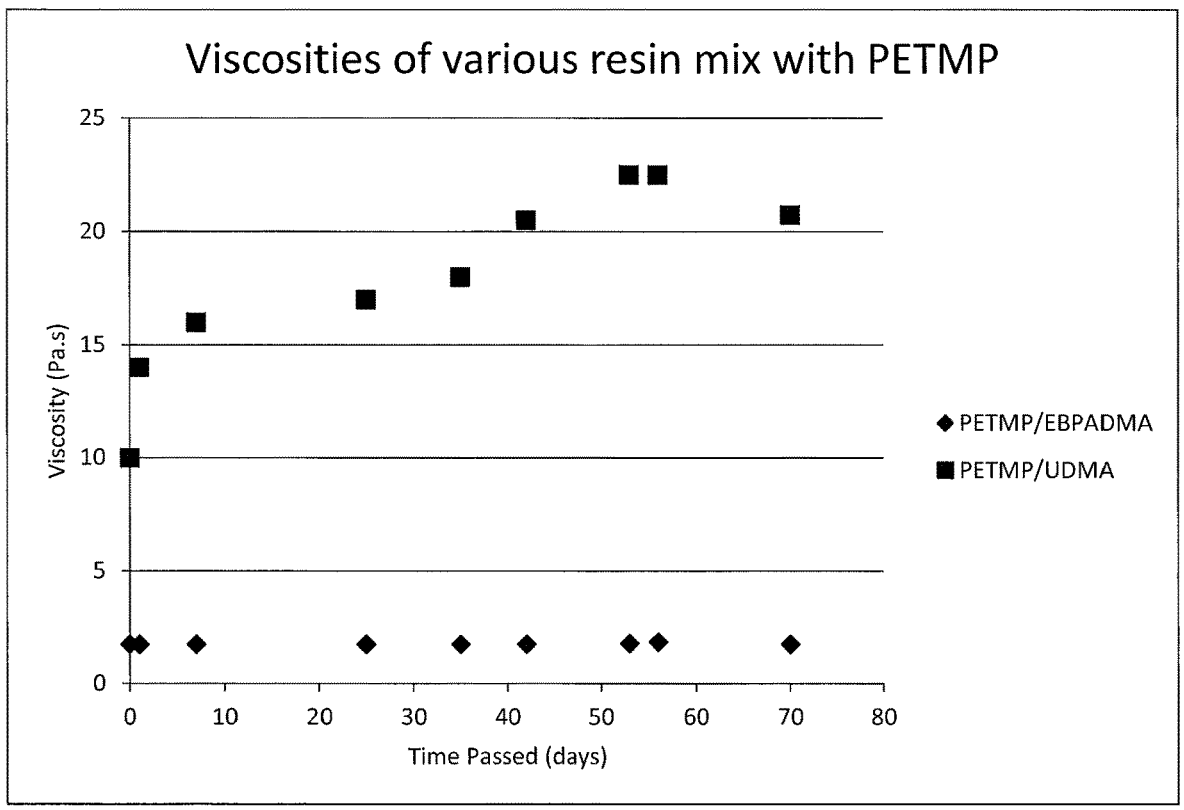
FIG. 13 demonstrates the aging effect on viscosity of various resin mixes with PETMP.
Figure 14:
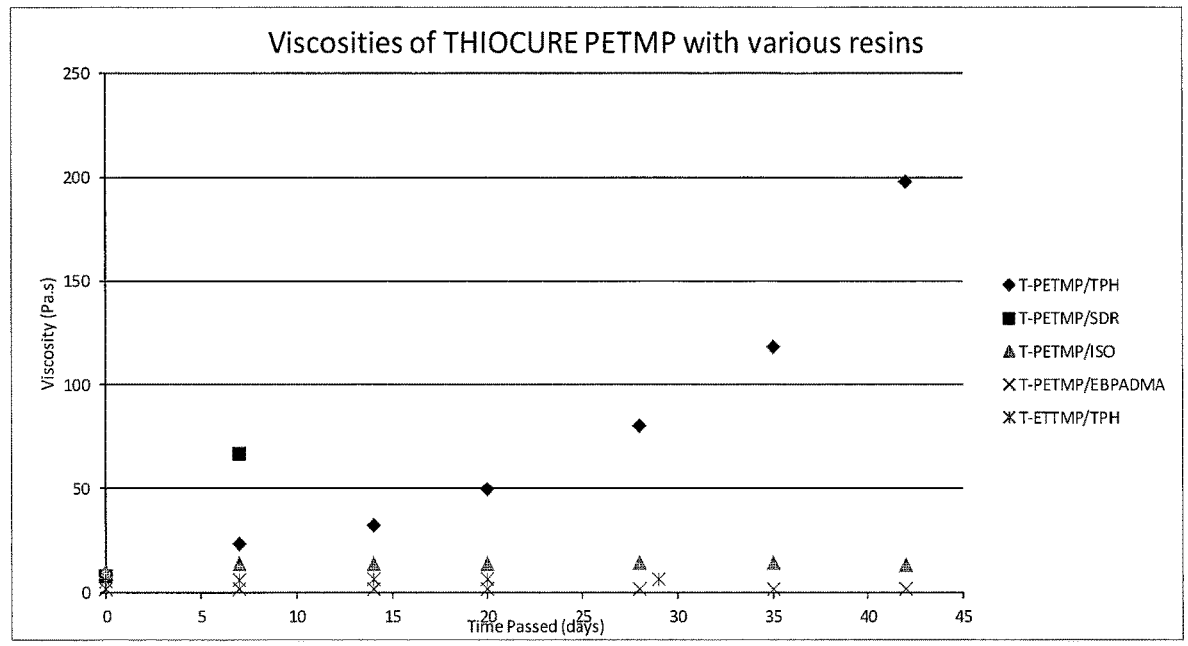
FIG. 14 demonstrates the aging effect on viscosity of THIOCURE PETMP with various resins.
Figure 15:
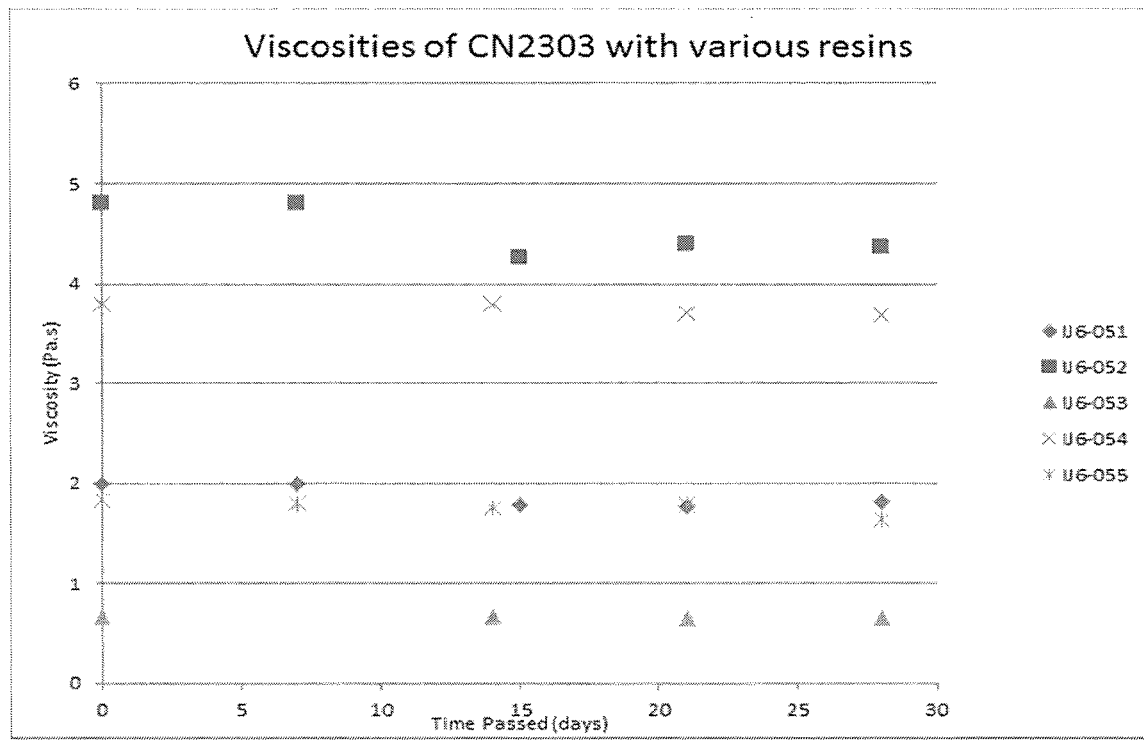
FIG. 15 demonstrates the aging effect on viscosity of TPH Resin, SDR Resin, Isosorbide Resin and EBPADMA as matrix resins in formulations for the catalyst composite paste, in which a hyperbranched polyester acrylate resin (NC2303 from Sartomer) was used as the polyene.

As shown in FIG. 13, EBPADMA/PETMP system is still remaining stable as aged for more than two months at RT. EBPADMA was found stable with THIOCURE PETMP as well as shown in FIG. 14. Thus it was chosen as the resin system for the base paste. To further evaluate the paste stability of such formulated composites, as shown in Table 2, TPH Resin, SDR Resin, Isosorbide Resin and EBPADMA were used as matrix resin in formulations for the catalyst composite paste, in which a hyperbranched polyester acrylate resin (NC2303 from Sartomer) was used as the polyene. These resulting paste/paste flowable composites were evaluated. As expected these formulated resins do demonstrate good stability as aged at room temperature (FIG. 15). Good mechanical properties were also found, see Table 4 and 5, from those pairs of formulated pastes containing SDR Resin (IJ6-057/060), EBPADMA (IJ6-058/060) and Isosorbide Resin (IJ6-059/060), respectively. However, all of these pairs of pastes would not cure well under LED irradiation. It was speculated there was an inefficient thiol/ene Michael addition reaction during the stage one between PETMP and NC2303. Thus there might leave excess PETMP as unreacted thiol prior to light curing, which would act as chain transfer agent that lead to poor crosslinking reaction under LED irradiation. It was expected that under halogen irradiation, however, a light-induced thiol/ene step-addition might occur so as to boost overall crosslinking reaction and no significant impact on mechanical property was found accordingly.

Figure 16:
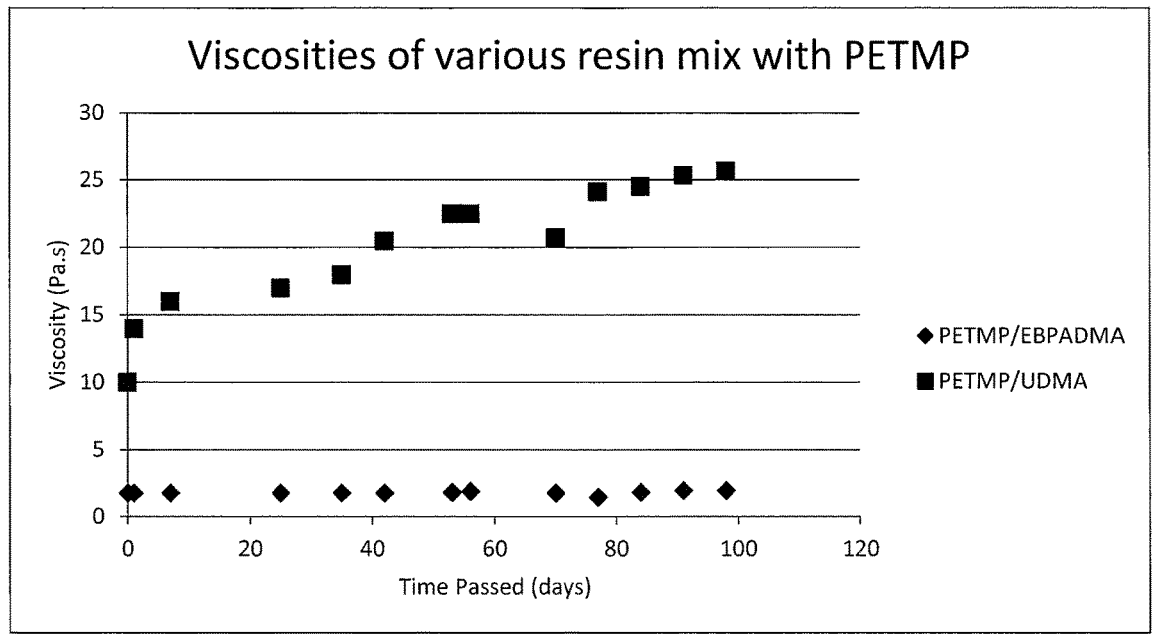
FIG. 16 demonstrates the aging effect on viscosity of a EBPADA/PETMP mix and a UDMA/PETMP mix.
Figure 17:
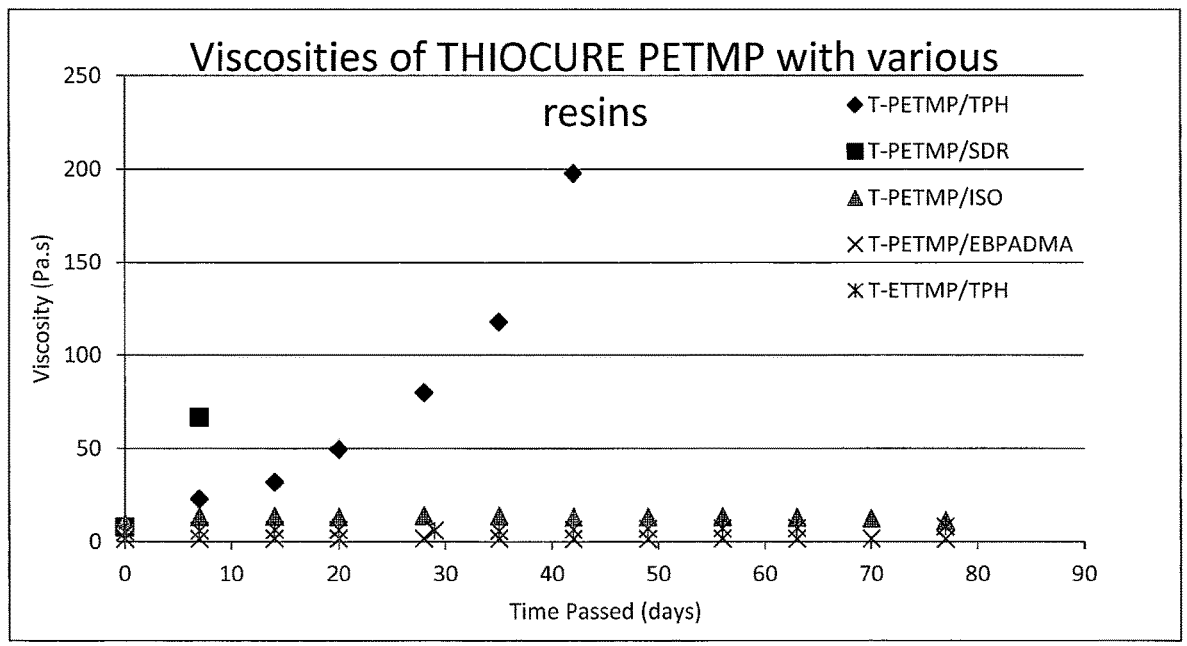
FIG. 17 demonstrates the aging effect on viscosity of various resins with PETMP or ETTMP.
Figure 18:
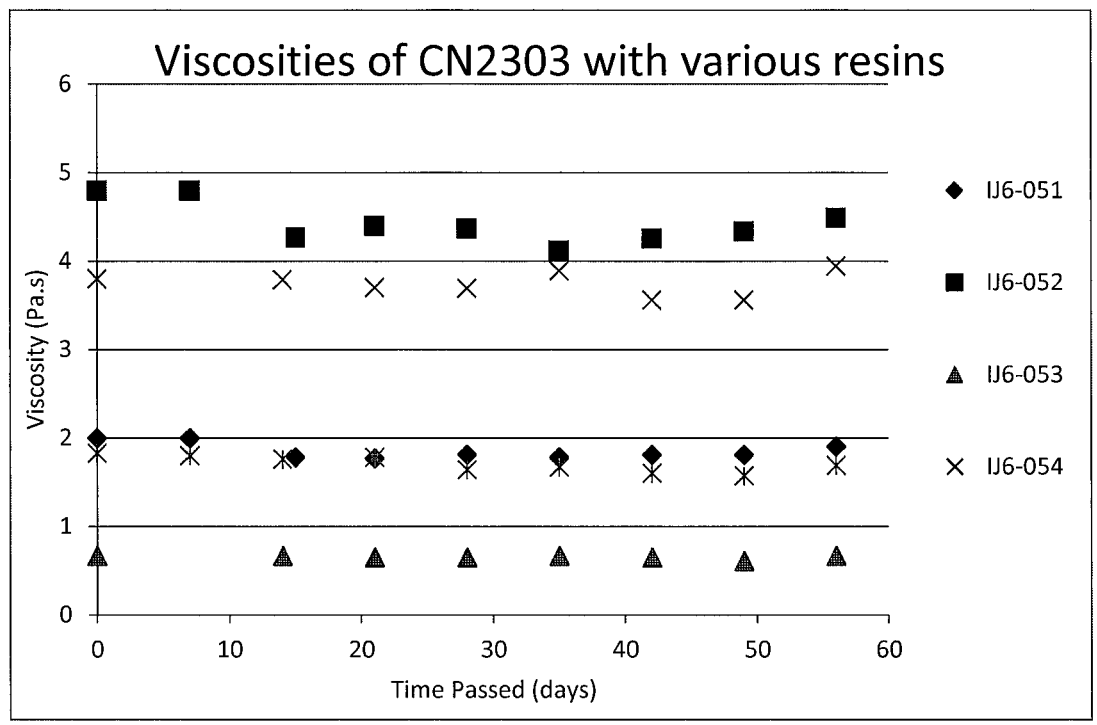
FIG. 18 demonstrates the aging effect on viscosity of various resins with PETMP.
Figure 19:
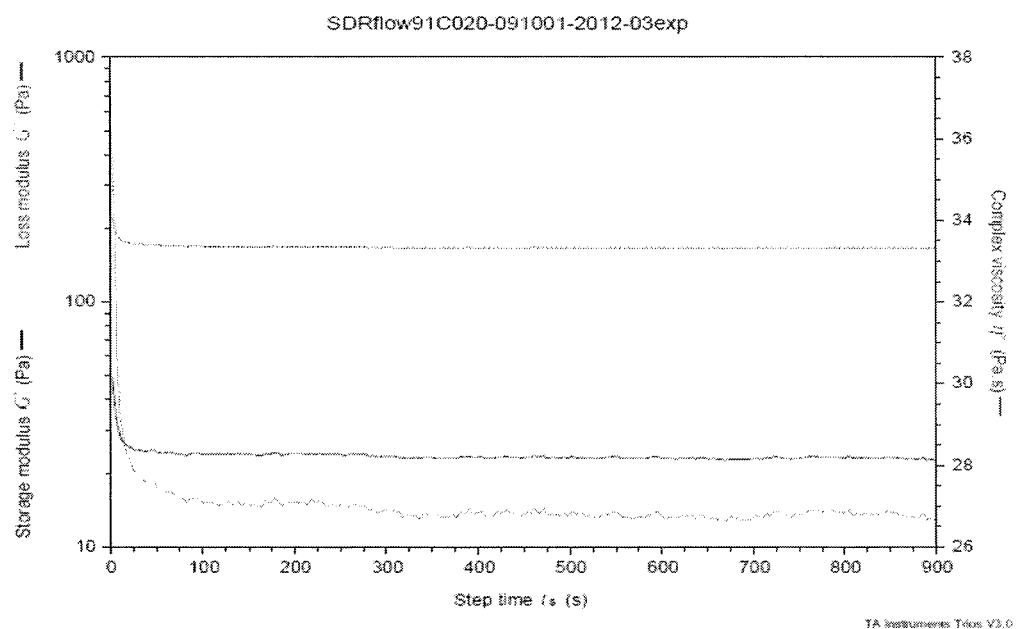
FIG. 19 demonstrates the oscillation profile of SureFil SDRflow®.
Figure 20:
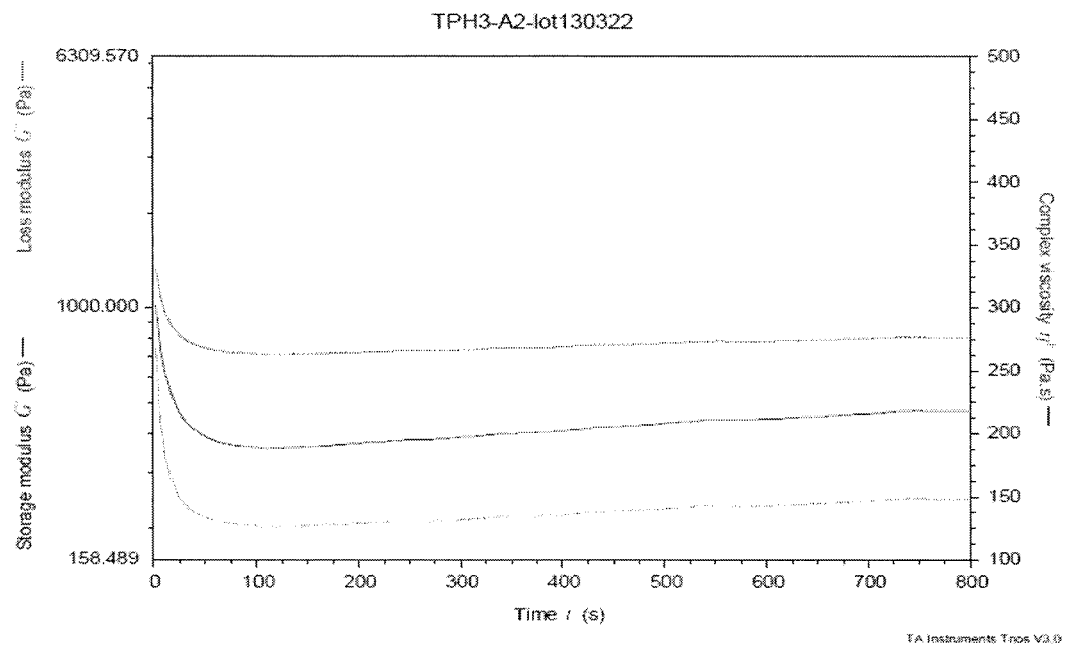
FIG. 20 demonstrates the oscillation profile of TPH3®.
Figure 21:
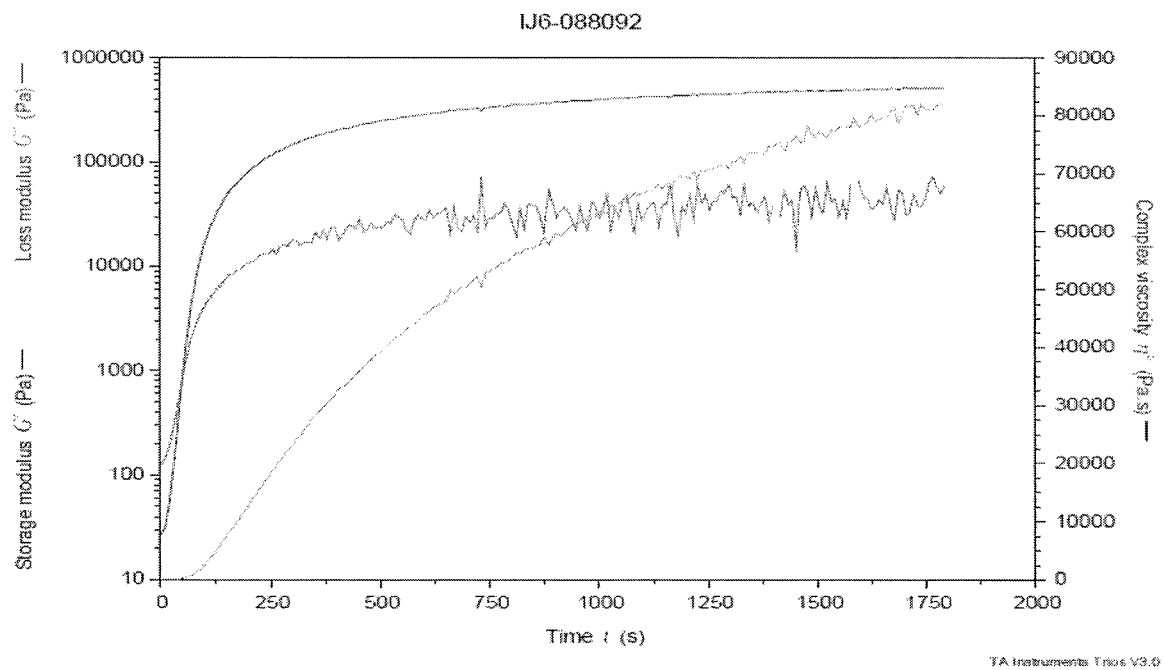
FIG. 21 demonstrates the oscillation profile for viscosity increasing flowable formulations.
Figure 22:
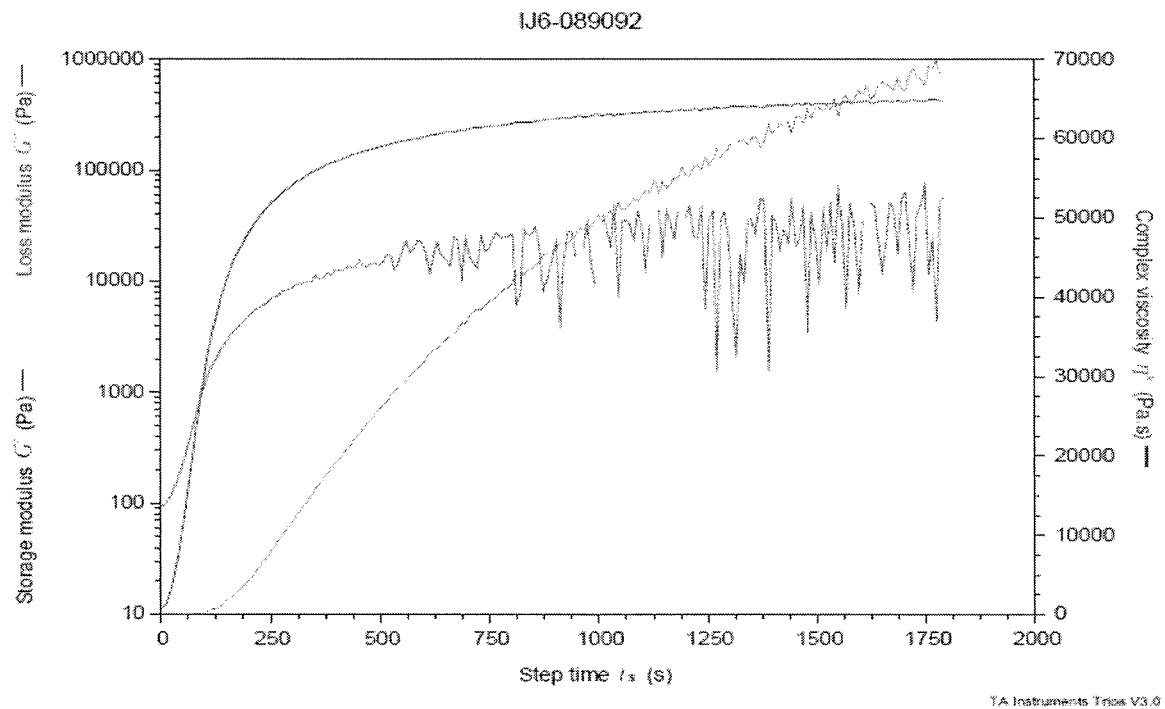
FIG. 22 demonstrates the oscillation profile for other viscosity increasing flowable formulations.
Figure 23:
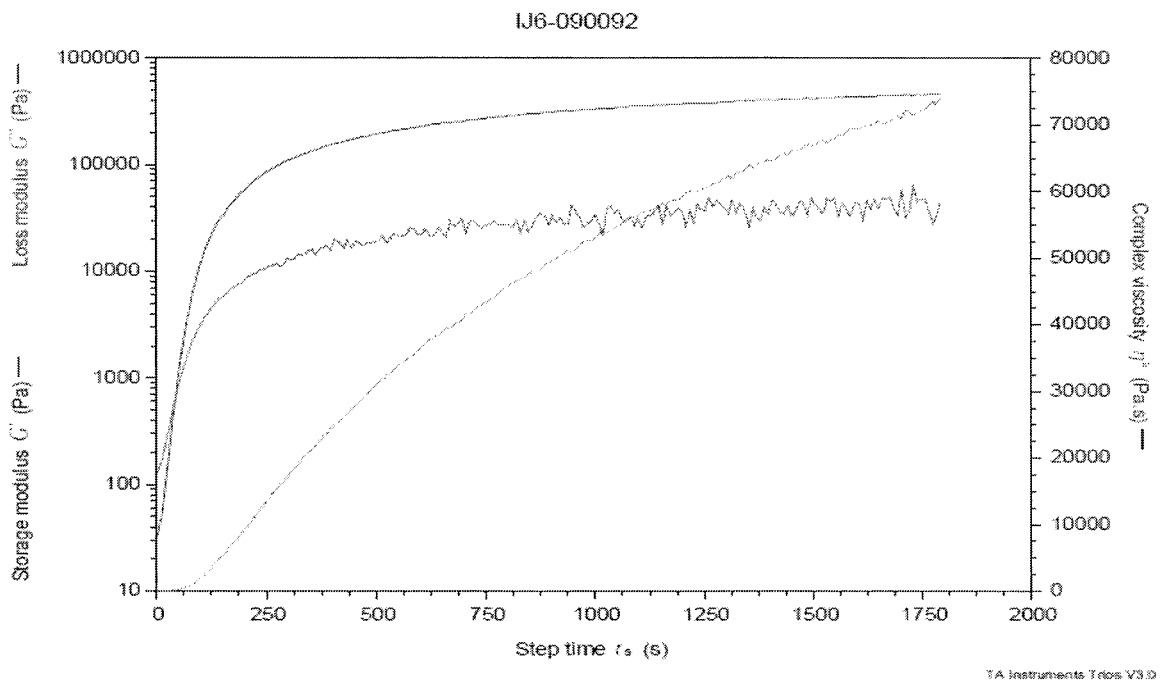
FIG. 23 demonstrates the oscillation profile for yet other viscosity increasing flowable formulations.
Figure 24:
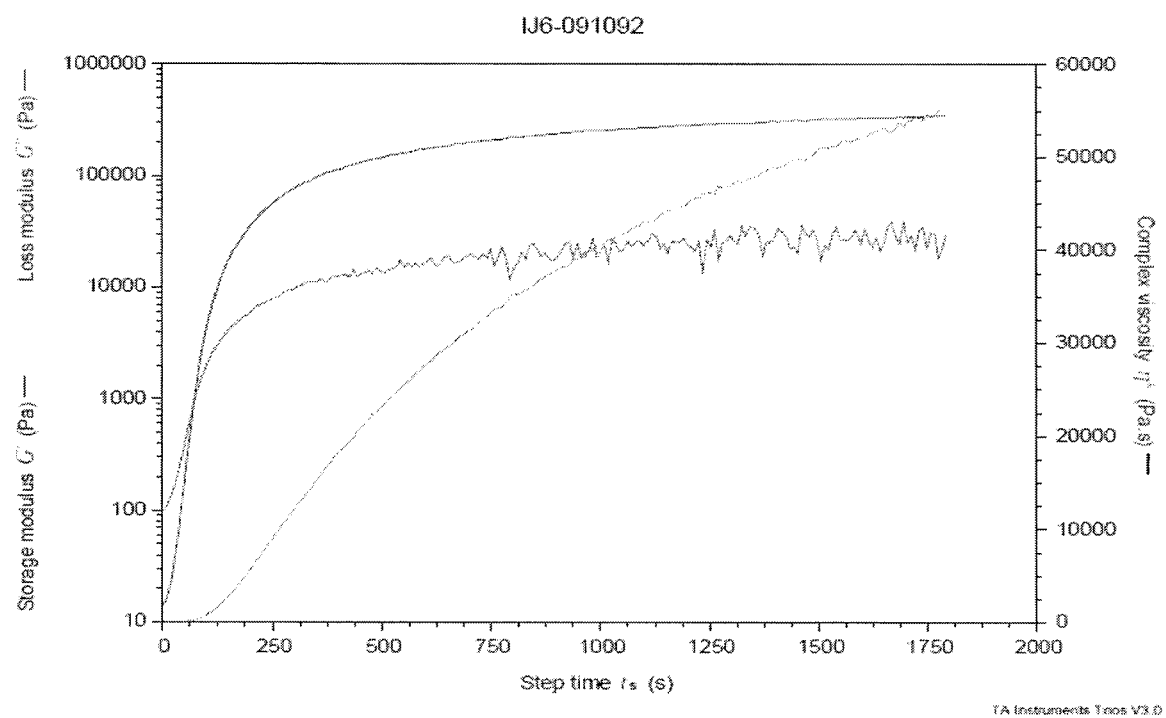
FIG. 24 demonstrates the oscillation profile for yet further viscosity increasing flowable formulations.
Figure 25:
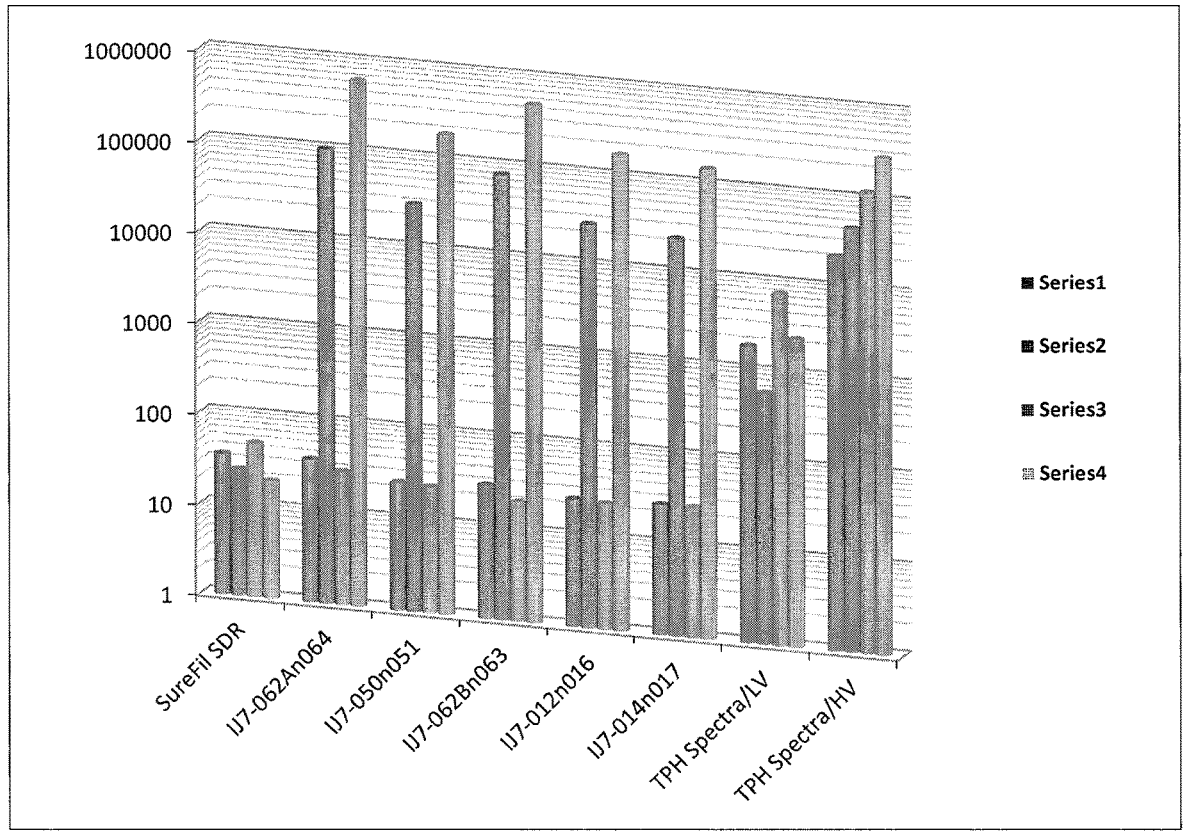
FIG. 25 demonstrates the viscosity and storage modulus for various viscosity increasing flowable composites.

Further as showed in FIG. 16, EBPADMA/PETMP system remains stable as aging for more than three months (98 days) at RT; In addition, Isosorbide resin and EBPADAM are stable with THIOCURE PETMP for more than two months (77 days) at RT. It was also interesting to note that TPH resin is stable with THIOCURE ETTMP though its blend with THIOCURE PETMP is not stable as showed in FIGS. 17 and 18. In Table 2, it is showed the compositions and mechanical properties of additional two series of catalyst pastes that contain both photoinitiators (CQ/LTPO) and thiol/ene catalyst (DBU) in resin blends of various methacrylate resins (TPH Resin, SDR Resin, Isosorbide Resin and EBPADMA) and acrylate resin (TCDCDA or SR295) were formulated and evaluated in an effort to optimize the composition for rapid initial viscosity increasing upon paste/paste mixing. Furthermore, FIGS. 19-24 showed the oscillation profiles of flowable composite (SureFil SDRflow® and universal composite (TPH3) and the experimental paste/paste-based viscosity-increasing flowables that are based on SR295 (IJ6-88/IJ6-92, IJ6-89/IJ6-92, IJ6-90/IJ6-92, and IJ6-91/IJ6-92, respectively). Obviously unlike the conventional composites, both SureFil SDRflow® or TPH3, a distinguished viscosity increasing was demonstrated as evident by the G'/G" crossover, which is ranged from 50" to 100" depending upon the resin composition. In Table 7-8, it is summarized the change of storage modulus (G'), loss modulus (G") and the complex viscosity ($\eta^*$). However, for those flowable pairs that are based on TCDCDA (IJ6-74/IJ6-80, IJ6-75/IJ6-80, IJ6-76/IJ6-80, and IJ6-77/IJ6-80), no such pronounced viscosity increasing was found, which might be attributed to the less effective of the diacrylate (TCDCDA) vs the Tetraacrylate (SR295) and the lower concentration of DBU.

TABLE 7

Rheological Property of Viscosity-increasing Flowable Composite

| Paste/Paste | Gel time @ 35° C., 175 Pa/1 Hz second | Complex Viscosity η*, Pa · s | | Storage Modulus G', Pa | | Loss Modulus G", Pa | |
|---|---|---|---|---|---|---|---|
| | | initial | @30 min | initial | @30 min | initial | @30 min |
| IJ6-088/IJ6-092 | 52 | 20 | 81950 | 25 | 500000 | 120 | 50000 |
| IJ6-089/IJ6-092 | 93 | 15 | 68045 | 12 | 400000 | 90 | 20000 |
| IJ6-090/IJ6-092 | 44 | 20 | 73830 | 35 | 450000 | 150 | 45000 |
| IJ6-091/IJ6-092 | 73 | 15 | 55030 | 15 | 300000 | 100 | 30000 |
| SureFil SDRflow | N/A | 37 | 27 | 50 | 25 | 220 | 180 |
| TPH3/A2 | N/A | 280 | 150 | 1000 | 400 | 1400 | 800 |

As discussed previously, it was discovered an effective viscosity—increasing for paste/paste flowable could be achieved upon mixing, as evident by the distinct modulus crossover for EBPADMA/PETMP and a variety of methacrylate resins paired SR295 in presence of DBU. However, no such crossover was found when same mathacryate resin paired with TCDCDA with same amount of DBU. It was speculated that further increase of DBU might boost the thiol/ene reaction for pronounced viscosity-increase. Thus in this month additional DBU, from 0.56% to 1.12% was used in same resin formulation with TCDCDA. Lower mechanical strength was resulted from all composites, which suggests potential negative impact of excess DBU on the free radical polymerization process: showed by both EBPADMA/PETMP and Methacrylate resins (TPH, SDR, EBPADMA and Isosorbide Resin)/TCTCDA if DBU is loaded in 1.12%. Indeed, no modulus crossover occurred for all these formulations.

As showed in Table 5, flowable composites based on EBPADMA/PETMP-EBPADMA/SR295 (IJ6-117/IJ6-118) were formulated by using Resodyn. The mechanical property of such resulting paste/paste composite got improved in comparison to those made via SpeedMix (IJ6-115/IJ6-116, see Table 5). Although the compounding process showed slight impact on the viscosity of the individual flowable, no effect was found on the gel-time during the course of viscosity-increasing process. Accordingly, higher polymerization stress was also resulted due to the reduced porosity in these pastes made via Resodyn. Again, the thiol/ene reaction remains fast, which led to fail in catching up the gel-time at 35° C.

Additional flowable formulations based on EBPADMA/PETMP-TPH Resin/SR295 and EBPADMA/PETMP-EBPADMA/SR295 in presence on reduced DBU (0.86%, wt/wt) and different photoinitiator systems (CQ/EDAB/LTPO vs CQ/LTPO) were formulated as showed Ross mixer and Resodyn (Table 5), respectively. Further improved mechanical properties of such paste/paste composite were evidently resulted for pastes made via Ross Mixer. No significant difference between those pastes containing different photoinitiator systems were found, which confirmed the effectiveness for the CQ/LTPO system in absence of EDAB. It was also found TPH Resin-based system tended to building up the viscosity quickly though there was relative longer gel time. As expected even higher polymerization stress of 3.65 MPa (IJ6-154/IJ6-156 in Table 5) and 3.84 MPa (IJ6-160/IJ6-162 in Table 5) were resulted, which featured in IJ6-154 and IJ6-160 any they derived from same resin, IJ6-149, composing of TPH Resin/SR295 and CQ/EDAB/DBU.

TABLE 8

Compositions and Properties of Flowable Composites@1 Hz

| Composite | Resin Mix %, wt/wt | Filler Mix IJ7-011 %, wt/wt | Initial Complex Viscosity@25° C. Pa | Initial Storage Modulus@25° C. G', Pa | Initial Loss Modulus@25° C. G", Pa |
|---|---|---|---|---|---|
| SureFil SDRflow | 999308 | K900473(58.2) | 40 | 50 | 220 |
| | | 912401(38.8) | 30 | 20 | 170 |
| | | 450489(3.0) | | | |
| | 31.93 | 68.07 | | | |
| TPH SPECTRA LV | 999445 | 999117(65.8) | 1,900 | 7,600 | 9,100 |
| | | 907645(32.9) | 600 | 2,700 | 2,900 |
| | | 431350(1.3) | | | |
| | 24.50 | 75.50 | | | |
| TPH SPECTRA HV | 999445 | 999117(65.8) | 22,600 | 122,300 | 71,800 |
| | | 907645(32.9) | 54,500 | 340,900 | 33,700 |
| | | 431350(1.3) | | | |
| | 22.75 | 77.25 | | | |
| IJ7-012 | IJ7-007 | 907645(40) | 70 | 115 | 425 |
| | | 907645(60) | 45 | 40 | 280 |
| Resodyn | 35 | 65 | | | |
| IJ7-013 | IJ7-008 | 907645(40) | 85 | 153 | 500 |
| | | 907645(60) | 50 | 60 | 300 |
| Resodyn | 35 | 65 | | | |
| IJ7-014 | IJ7-007 | 907645(40) | 85 | 155 | 500 |
| | | 907645(60) | 50 | 45 | 300 |

TABLE 8-continued

Compositions and Properties of Flowable Composites@1 Hz

| Composite | Resin Mix %, wt/wt | Filler Mix IJ7-011 %, wt/wt | Initial Complex Viscosity@25° C. Pa | Initial Storage Modulus@25° C. G', Pa | Initial Loss Modulus@25° C. G", Pa |
|---|---|---|---|---|---|
| Resodyn | 35 | 65 | | | |
| IJ7-015 | IJ7-008 | 907645(40) | 75 | 125 | 450 |
| | | 907645(60) | 50 | 45 | 300 |
| Resodyn | 35 | 65 | | | |
| IJ7-016 | IJ7-009 | 907645(40) | 55 | 60 | 150 |
| | | 907645(60) | 20 | 30 | 110 |
| Resodyn | 35 | 65 | | | |
| IJ7-017 | IJ7-010 | 907645(40) | 25 | 60 | 155 |
| | | 907645(60) | 20 | 30 | 110 |
| Resodyn | 35 | 65 | | | |

Fillers:
1. BAFG/907445: silanated Ultrafine EG9726, 0.92-0.96 micron
2. BAFG/907446: silanted As-received EG9726, 4-7 microns

TABLE 9

Compositions and Properties of Flowable Composites@1 Hz

| Composite | Resin Mix %, wt/wt | Filler Mix %, wt/wt | Initial Complex Viscosity@35° C. Pa | Initial Storage Modulus@35° C. G', Pa | Initial Loss Modulus@35° C. G", Pa |
|---|---|---|---|---|---|
| IJ6-115 | IJ6-113 | 907645(55) | 11 | 12 | 67 |
| | | 907646(40) | 8 | 8 | 50 |
| | | OX-50(5) | | | |
| SpeedMix | 40 | 60 | | | |
| IJ6-116 | IJ6-114 | 907645(55) | 21 | 45 | 125 |
| | | 907646(40) | 15 | 25 | 92 |
| | | OX-50(5) | | | |
| SpeedMix | 40 | 60 | | | |
| IJ6-117 | IJ6-113 | 907645(55) | 8 | 6 | 50 |
| | | TPM 1(40) | 7 | 4 | 40 |
| | | OX-50(5) | | | |
| SpeedMix | 40 | 60 | | | |
| IJ6-118 | IJ6-114 | 907645(55) | 17 | 30 | 104 |
| | | TPM 1(40) | 10 | 12 | 63 |
| | | OX-50(5) | | | |
| SpeedMix | 40 | 60 | | | |
| IJ6-139 | IJ6-113 | 907645(55) | 10 | 10 | 63 |
| | | 907646(40) | 9 | 8 | 53 |
| | | OX-50(5) | | | |
| Resodyn | 40 | 60 | | | |
| IJ6-140 | IJ6-114 | 907645(55) | 18 | 32 | 107 |
| | | 907646(40) | 13 | 18 | 79 |
| | | OX-50(5) | | | |
| Resodyn | 40 | 60 | | | |
| IJ6-141 | IJ6-113 | 907645(55) | 7 | 4 | 41 |
| | | TPM 1(40) | 6 | 3 | 36 |
| | | OX-50(5) | | | |
| Resodyn | 40 | 60 | | | |
| IJ6-142 | IJ6-114 | 907645(55) | 12 | 14 | 75 |
| | | TPM 1(40) | 9 | 7 | 55 |
| | | OX-50(5) | | | |
| Resodyn | 40 | 60 | | | |

Fillers:
1. 999141: silanted OX-50,
2. 907445: silanted UltraFine EG9726, 0.92-0.96 micron
3. 907446: silanted As-received EG9726, 4-7 microns
4. TPM1: 130813_1R(YC9-129), 20.3 microns; BET/4.0

TABLE 10

Compositions and Initial Rheological Properties of Viscosity-increasing Flowable Composites

| Composite | Initial Complex Viscosity@25° C. Pa | Initial Storage Modulus@25° C. Pa | Initial Loss Modulus@25° C. Pa | Time at Gel Point@25° C. Second | Modulus at Gel Point@25° C., Pa. |
|---|---|---|---|---|---|
| RossMixer IJ6-152n156 | 34 | 27 | 214 | 98 | 1,508 |
| RossMixer IJ6-153n156 | 20 | 17 | 122 | 48 | 750 |
| RossMixer IJ6-154n156 | 28 | 22 | 177 | 84 | 1,174 |
| RossMixer IJ6-155n156 | 17 | 16 | 108 | 103 | 715 |
| Resodyn IJ6-158n162 | 25 | 22 | 154 | 139 | 1,345 |
| Resodyn IJ6-159n162 | 17 | 16 | 108 | 84 | 755 |
| Resodyn IJ6-160n162 | 24 | 16 | 150 | 134 | 1,266 |
| Resodyn IJ6-161n162 | 16 | 15 | 101 | 97 | 733 |
| Resodyn IJ7-012n016 | 25 | 25 | 160 | 150 | 997 |
| Resodyn IJ7-013n016 | 29 | 28 | 180 | 162 | 1099 |
| Resodyn IJ6-014n017 | 27 | 28 | 171 | 160 | 1034 |
| Resodyn IJ6-015n017 | 25 | 27 | 157 | 210 | 1056 |
| Resodyn IJ7-050n051 | 26 | 25 | 162 | 82 | 1078 |
| Resodyn IJ7-052n053 | 57 | 63 | 356 | N/A | N/A |
| Resodyn IJ7-062An063 | 30 | 21 | 185 | 77 | 1225 |
| Resodyn IJ7-062Bn064 | 30 | 38 | 240 | 78 | 1585 |

TABLE 11

Compositions and 15 min-set Rheological Properties of Viscosity-increasing Flowable Composites

| Composite | Composite A | Composite B | Complex Viscosity@25° C. Pa | Storage Modulus@25° C. Pa | Loss Modulus@25° C. Pa |
|---|---|---|---|---|---|
| RossMixer IJ6-152n156 | IJ6-152 | IJ6-156 | 35,300 | 218,960 | 35,450 |
| RossMixer IJ6-153n156 | IJ6-153 | IJ6-156 | 51,830 | 321,500 | 51,800 |
| RossMixer IJ6-154n156 | IJ6-154 | IJ6-156 | 52,960 | 326,100 | 66,190 |
| RossMixer IJ6-155n156 | IJ6-154 | IJ6-156 | 38,450 | 239,000 | 35,350 |
| Resodyn IJ6-154n156 | IJ6-158 | IJ6-162 | 50,220 | 312,960 | 40,490 |
| Resodyn IJ6-155n156 | IJ6-159 | IJ6-162 | 53,390 | 331,540 | 51,190 |
| Resodyn IJ6-160n162 | IJ6-160 | IJ6-162 | 50,540 | 314,650 | 43,090 |
| Resodyn IJ6-161n162 | IJ6-161 | IJ6-162 | 50,760 | 316,400 | 40,060 |

It was surprisingly found that the individual catalyst pastes made from RossMixer got gelled by after aging at RT for a couple of weeks though the polythiol base paste made from RossMixer remains stable. However, it was also found that same catalyst pastes made from Resodyn also remain stable, which should be attributed to the thermal degradation of the acrylate resin (SR295). Thus such findings should also suggest that Resodyn process is a better option for compounding those heat-sensitive compositions.

Thus it is concluded that

Thiol-ene chemistry could be viable approach to viscosity-increasing system by using a superbase, such as DBU, for rapid network formation at ambient temperature; Extra DBU do accelerate the rate of thiol-ene reaction for the viscosity-increasing compositions, but it might be also related to the reduced mechanical properties. Further investigation is needed to clarify the negative factor of DBU and porosity for the high filler loaded flowable compositions.

Polyacrylate resins, such as TCDCDA or SR295, could be used in the catalyst pastes, in combination with conventional methacrylate resins, such as TPH resin, SDR resin, Isosorbide resin and UDMA. No significant advantage for those high purity of polythiols (THIOCURE PETMP or THIOCURE ETTMP 1300) in stabilizing those urethane-based methacrylated resins (TPH resin, SDR resin, Isosorbide resin or UDMA).

However, is was discovered that only urethane-free methacrylate resins, such as EBPADMA, would be the chemically compatible with polythiol (PETMP). It was also found that additional additives, like TPP and L-Gallate were effective in stabilizing TPH resin or SDR resin, respectively.

Improved mechanical properties were achieved by compounding the individual flowable composite in Ross Mixer or Resodyn due to the reduced porosity. But detsablized base phase was found as a result of mixing by RossMixer under reduced pressure.

I claim:

1. A two-component flowable dental composition capable of being cured in a two-stage curing process, said dental composition comprising: (a) a base paste comprising a polythiol and a methacrylate, and (b) a catalyst paste comprising a polyene, a methacrylate resin, a photoinitiator and a base catalyst;

wherein the polyene is selected from the group consisting of tricyclo[5.2.1.0$^{2,6}$]decanedimethanol diacrylate, pentaerythritol tetraacrylate and polyacrylates;

wherein the base catalyst is capable of promoting thiol-ene Michael-addition at room temperature upon the base paste/catalyst paste mixing in stage one of the two-stage curing process; and the photoinitiator is capable of promoting radical addition in stage two of the two stage curing process.

2. The dental composition according to claim 1, wherein the base paste includes ethoxylated bisphenol A dimethacrylate or tri(ethylene glycol) dimethacrylate.

3. The dental composition according to claim 1, wherein the polythiol includes pentaerythritol tetra(3-mercaptopropionate) or ethoxylated-trimethylolpropan tri(3-mercaptopropionate.

4. The dental composition according to claim 1, wherein the photoinitiator includes camphorquinone, 2,4,6-trimethylbenzoyl diphenylphosphine oxide or mixtures thereof.

5. The dental composition according to claim 1, wherein base paste further comprises an additive.

6. The dental composition according to claim 5, wherein the additive includes lauryl gallate, pyrogallol, tris (2,4-di-tert-butylphenyl)phosphite or triphenylphosphite.

7. The dental composition according to claim 1, wherein the composition is capable of being further polymerized by irradiation of a light of from 320 nm to 480 nm.

8. The dental composition according to claim 1, wherein the base paste and catalyst paste further includes a glass filler in a concentration of from 10 to 70 weight percent based on the total weight of the composition.

9. The dental composition according to claim 1, wherein the base paste and catalyst paste further comprises a nano-silica.

10. The dental composition according to claim 1, wherein the base catalyst is selected from the group consisting of triethyl amine, 1,8-diazabicyclo[5,4,0] undec-7-ene, and 1,4-diazabicyclo[2,2,2]-octane.

11. The dental composition according to claim 1, wherein the flowable dental composition is capable of achieving controlled viscosity increase upon base paste/catalyst paste mixing due to thiol-ene Michael addition prior to light irradiation.

12. A flowable composite produced by curing the two-component flowable dental composition according to claim 1 in the two-stage curing process.

* * * * *